(12) United States Patent
Heeney et al.

(10) Patent No.: US 7,700,643 B2
(45) Date of Patent: Apr. 20, 2010

(54) POLYMERISABLE THIENO[3,2-B]THIOPHENES

(75) Inventors: Martin Heeney, Southampton (GB); Weimin Zhang, Southampton (GB); Iain McCulloch, Southampton (GB)

(73) Assignee: Merck Patent GmbH, Darmstadt (DE)

( * ) Notice: Subject to any disclaimer, the term of this patent is extended or adjusted under 35 U.S.C. 154(b) by 610 days.

(21) Appl. No.: 11/570,306

(22) PCT Filed: May 13, 2005

(86) PCT No.: PCT/EP2005/005292
§ 371 (c)(1), (2), (4) Date: Dec. 8, 2006

(87) PCT Pub. No.: WO2005/121150
PCT Pub. Date: Dec. 22, 2005

(65) Prior Publication Data
US 2007/0246704 A1    Oct. 25, 2007

(30) Foreign Application Priority Data
Jun. 9, 2004    (EP) ................... 04013598

(51) Int. Cl.
*A61K 31/381* (2006.01)
*C07D 409/14* (2006.01)
(52) U.S. Cl. ........................ 514/444; 549/59
(58) Field of Classification Search ........... 514/444; 549/59
See application file for complete search history.

(56) References Cited

U.S. PATENT DOCUMENTS

| 5,677,095 A | 10/1997 | Kikuchi et al. |
| 6,800,763 B2 | 10/2004 | Farrand et al. |

FOREIGN PATENT DOCUMENTS

| DE | 196 39 381 A1 | 3/1998 |
| DE | 19639381 | 3/1998 |
| EP | 0 466 094 A | 1/1992 |
| EP | 0466094 | 1/1992 |
| EP | 1275650 | 6/2002 |
| EP | 1 275 650 A | 1/2003 |
| EP | 1 510 535 A | 3/2005 |
| EP | 1510535 | 3/2005 |

OTHER PUBLICATIONS

Nakayama, Juzo et al., Tetrahedron, 1996, pp. 471-488, vol. 52, No. 2.
Zhang, X. et al. J. Org. Chem., 2003, pp. 9813-98915, vol. 68.
Abstract RN265654-20-4, JP200 122068 A Fuji Electric Co., Apr. 28, 2000, p. 10-12, Database HCAPLUS, Online, ACS, Database accession No. 200 :274534.

Takahashi K. et al., 2, 6-BIS(3, 5-Di-T-Butyl-4-Oxo-Clyclohexa-2, 5-Dien-1-Ylidene)-2,5-Dihydr 0-1, 4-Dithiapentalene : A New Class of Amphorteric Multi-Stage Redox Systems Consisting of Both The Wurster and The Weitz Types, Journal of the Chemical Society, 1990, pp. 1196-1198.
Wichern J. 3et al., Hight Electro-optic Response in Polymers Doped With Novel Chromophores With Good Thermal and Orientational Stability, Optical Materials, Elsevier Science, Jan. 1998, pp. 280-286, vol. 9, No. 1-4. Amsterdam, NL.
Rutherford D. R. et al., Poly(2,5-Ethynylenethiophenediylethynylenes, Related Heteroaromatic Analogues, and Poly(Thieno(3,2-B)Thiophenes), American Chemical Society, Apr. 27, 1992, pp. 2294-2306, vol. 25, No. 9, Easton, US.
Door, M. et al., Proc. Of Spie-the Internat. Soc. For Optical Eng., 1995, pp. 105-115, vol. 2527.
Lim, Eunhee et al Macromolecules, 2002, pp. 132-135, vol. 417.
Paik, Kyung Lim et al., Thin Solid Films, 2002, vol. 417, pp. 132-135.
Danieli R. et al., Synthetic Metals, 1986, pp. 325-328, vol. 13.
Database WPI, Week 200270 Derwent Publication Ltd. Abstract KR 2002 027 935A, Apr. 15, 2002.
Nakayama, et al. "Synthesis and Characterization of Dimers, Trimers, and Tetramers of 3,6-Dimethylthieno[3,2-b]thiophene and ..." Tetrahedron, 52(2): 471-488 (1996).
Zhang, et al. "Effect of Ring Fusion on the Electronic Absorption and Emission Properties of Oligothiophenes" J. Org. Chem. 68(25):9813-9815 (2003).
Abstract RN265654-20-4, JP2000122068 A Fuji Electric Co., Apr. 28, 2000, p. 10-12, Database HCAPLUS, Online, ACS, Database accession No: 200:274534.
Takahashi, et al. "2,5 Bis(3,5-di-t-butyl-4-oxo-cyclohexa-2,5-dien-1-ylidene)- 2,5-dihydro-1,4-dithiapentalene: A New Class of Amphoteric Multi-stage Redox Systems consisting of Both the Wurster and the Weitz Types" J. Chemical Society, Chemical Communications, pp. 1196-1198 (1990).
Cazenobe, et al. "High electro-optic response in polymers doped with novel chromophores with good thermal and orientational stability" Optical Materials 9:280-285 (1998).
Rutherford, et al. "Poly(2,5-ethynylenethiophenediylethynylenes), Related Heteroaromatic Analogues, and Poly(thieno[3,2-b]thiophenes). Synthesis and Thermal and Electrical Properties" Macromolecules 25(9):2294-2306 (1992).
Dörr, et al. "High Tg NLO-polymers by functionalization of reactive precursors" SPIE, 2527:105-115 (1995).

(Continued)

*Primary Examiner*—Taofiq A Solola
(74) *Attorney, Agent, or Firm*—Millen, White, Zelano, Branigan, P.C.

(57) ABSTRACT

The invention relates to novel polymerisable thieno[3,2-b] thiophenes, to their use as semiconductors or charge transport materials, in optical, electro-optical or electronic devices like for example liquid, crystal displays, optical films, organic field effect transistors (FET or OFET) for thin film transistor liquid crystal displays and integrated circuit devices such as RFID tags, electroluminescent devices in flat panel displays, and in photovoltaic and sensor devices, and to field effect transistors, light emitting devices or ID tags comprising the novel compounds.

26 Claims, No Drawings

OTHER PUBLICATIONS

Lim, et al. "Synthesis and Characterization of a New Light-Emitting Fluorene-Thieno[3,2-b]thiophene-Based Conjugated Copolymer" Macromolecules 36(12):4288-4293 (2003).

Paik, et al. "Synthesis and luminescent properties of novel silicon-based (p-phenylene) related polymers containing oxadiazole units for PLED" Thin Solids Films 417:132-135 (2002).

Danieli, et al. "Optical, Electrical and Electrochemical Characterization of Electrosynthesized Polythieno(3,2-b)thiophene" Synthetic Metals 13:325-328 (1986).

Abstract KR 2002027935, Database WPI, Week 200270 Derwent Publication Ltd. Apr. 15, 2002, Database accession No: 2002-652360[70].

Abstract KR2027935A, The Delphion Integrated View: INPADOC Record (2002).

Fuller, et al. "Thienothiophenes. Part 2. Synthesis, metallation and bromine→lithium exchange reactions of thieno[3,2-b]thiophene and its polybromo derivatives" J. Chem.Soc., Perkin Trans. 1, pp. 3465-3470 (1997).

POLYMERISABLE THIENO[3,2-B]THIOPHENES

FIELD OF INVENTION

The invention relates to novel polymerisable Thieno[3,2-b]thiophenes. The invention further relates to their use as semiconductors or charge transport materials, in optical, electro-optical or electronic devices like for example liquid crystal displays, optical films, organic field effect transistors (FET or OFET) for thin film transistor liquid crystal displays and integrated circuit devices such as RFID tags, electroluminescent devices in flat panel displays, and in photovoltaic and sensor devices. The invention further relates to a field effect transistor, light emitting device or ID tag comprising the novel compounds.

BACKGROUND AND PRIOR ART

In prior art polymers consisting of repeating thiophene units have been reported to show good performance as charge transporting materials in FET applications. For example, regioregular poly(3-alkyl)thiophene for example has demonstrated one of the highest recorded mobilities to date for a polymer (Sirringhaus et al., Science, 1998, 280, p 1741). Also, polythiophene analogues as disclosed for example in EP 1 327 646 A1, EP 1 327 647 A1, EP 1 329 474 A1 or EP 1 329 475 A1 containing different numbers and regioisomers of alkyl-thiophenes exhibit reasonable charge carrier mobilities.

This performance is thought to be due to two factors. Firstly the arrangement of the alkyl side-chains on the polymer backbone allows the polymers to self-organise into well-ordered structures on coating from solution. This facilitates the hopping mechanisms that dominate charge transport. Secondly the presence of sulfur atoms in the polymer backbone has been shown to be beneficial to charge transport. The exact mechanism is not known, but it is speculated that interaction of the sulfur d-orbitals on adjacent polymer chains facilitates the charge hopping mechanism.

However, the polymers disclosed in the above prior art documents do only show charge carrier mobilities of not more than 0.1 $cm^2V^{-1}s^{-1}$. Also, the materials of prior art often show only limited solubility which is a disadvantage when processing the polymers for the manufacture of semiconductor devices like thin film transistors (TFT) or field effect transistors (FET).

Therefore, further enhancement of the charge mobility and solubility of organic polymers is desired in order to enable transistor performance.

It was an aim of the present invention to provide new organic materials for use as semiconductors or charge transport materials, which are easy to synthesise, have high charge mobility and good processibility. Especially the materials should be easily processible to form thin and large-area films for use in semiconductor devices. Also, the materials should be oxidatively stable, but retain or even improve the desired electrical properties.

The inventors of the present invention have found that materials based on thieno[3,2-b]thiophene (1) (TT)

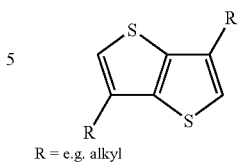

R = e.g. alkyl in particular monomers comprising a mesogenic core with a TT group and one or more polymerisable groups attached thereto, show improved charge carrier mobility whilst maintaining desirable solution processable properties.

In prior art there are no reported examples of molecules containing TT groups that exhibit LC behaviour. Nakayama et al., Tetrahedron 1996, 52, p 471 report dimers, trimers and tetramers of 3,6-dimethyl-TT as shown below.

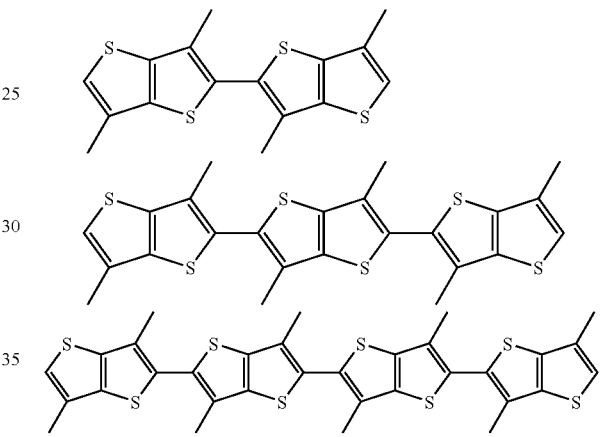

However, these materials are neither designed nor reported to exhibit LC behaviour, and additionally are reported to exhibit low solubility. No electronic behaviour is reported. High mobility is not expected with these materials because of the steric twisting, caused by the interaction of the adjacent methyl groups in the 3 and 6 positions.

Zhang and Matzger, J. Org. Chem. 2003, 68, p 9813-0815, disclose TT compounds as shown below.

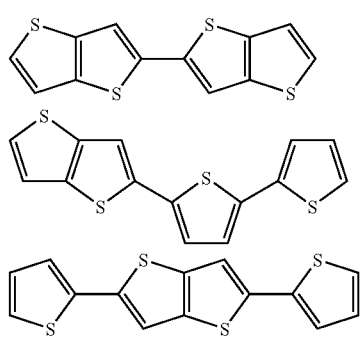

These molecules are unsubstituted and do not exhibit LC behaviour. No electrical data is reported.

WO 99/12989 discloses oligomers and polymers comprising two or more fused thiophene rings which may be substituted or unsubstituted for use in TFTs and FETs. However, there is no specific disclosure of mesogenic TT monomers with polymerisable terminal groups or their preparation.

EP 1 275 650 A2 discloses compounds comprising one or more fused thiophene rings and polymerisable groups, but does not explicitly disclose compounds according to the present invention.

Thus, another aim of the invention was to provide thieno [3,2-b]thiophene (TT) materials that are more easily processible in the manufacture of semiconductor devices, have higher stability and allow easier synthesis also at large scale compared to TT materials of prior art.

It was found that the above aims can be achieved by providing compounds according to the present invention.

SUMMARY OF THE INVENTION

The invention relates to compounds comprising at least one thieno[3,2-b]thiophene-2,5-diyl (TT) group and at least one group that is capable of participating in a polymerisation reaction or capable of being grafted to a polymer backbone (polymerisable or reactive group), or a protected form of said polymerisable group, preferably to mesogenic or liquid crystalline compounds of this type.

The invention further relates to linear and crosslinked polymers obtained from the TT compounds as described above and below.

The invention further relates to a polymerisable liquid crystal material comprising one or more TT compounds as described above and below, and optionally comprising one or more further polymerisable compounds, wherein at least one of the TT compounds and/or the further polymerisable compounds is mesogenic or liquid crystalline.

The invention further relates to anisotropic polymer films with charge transport properties obtainable from one or more TT compounds or polymerisable liquid crystal materials as described above and below that are aligned in the liquid crystal phase into macroscopically uniform orientation and polymerised or crosslinked to fix the oriented state.

The invention further relates to a semiconductor or charge transport material, component or device comprising at least one compound, polymerisable material or polymer as defined above and below.

The invention further relates to the use of compounds, polymerisable materials and polymers according to the invention as charge-transport, semiconducting, electrically conducting, photoconducting or light-emitting material in optical, electrooptical or electronic components or devices, organic field effect transistors (OFET), integrated circuitry (IC), thin film transistors (TFT), flat panel displays, radio frequency identification (RFID) tags, electroluminescent or photoluminescent devices or components, organic light emitting diodes (OLED), backlights of displays, photovoltaic or sensor devices, charge injection layers, Schottky diodes, planarising layers, antistatic films, conducting substrates or patterns, electrode materials in batteries, photoconductors, electrophotographic applications, electrophotographic recording, organic memory devices, alignment layers, or for detecting and discriminating DNA sequences.

The invention further relates to an optical, electrooptical or electronic device, FET, integrated circuit (IC), TFT, OLED or alignment layer comprising a semiconducting or charge transport material, component or device according to the invention.

The invention further relates to a TFT or TFT array for flat panel displays, radio frequency identification (RFID) tag, electroluminescent display or backlight comprising a semiconducting or charge transport material, component or device or a FET, IC, TFT or OLED according to the invention.

The invention further relates to a security marking or device comprising a FET or an RFID tag according to the invention.

DETAILED DESCRIPTION OF THE INVENTION

Especially preferred are compounds comprising a mesogenic core that comprises at least one thieno[3,2-b] thiophene-2,5-diyl (TT) group and is linked, optionally via spacer groups, to one or more, preferably one or two polymerisable or reactive groups.

Compounds comprising a TT group and a thieno[2,3-b] thiophene-2,5-diyl group

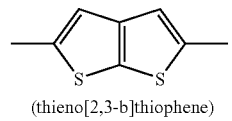

(thieno[2,3-b]thiophene)

that is optionally substituted in 3- and/or 4-position, are preferably excluded from the present invention.

The compounds according to the invention are especially useful as charge transport semiconductors because they have high carrier mobilities. One reason for this improvement in charge carrier mobility is the enhanced planarity and conjugation of the fused ring system, in addition to the higher concentration of sulfur atoms per unit length. For example TT has three double bonds and two sulfur atoms per molecules, whilst thiophene has two double bonds and one sulfur atom, and 2,2-bithiophene has four double bonds and two sulfur atoms per molecule. This results in mesogens that show higher charge carrier mobility in comparison to systems not containing these units (or containing non-fused thiophene rings). Furthermore, the compounds of the present invention with a thieno[2,3-b]thiophene-2,5-diyl group have a linear configuration, which helps to promote desirable mesophase behaviour.

Combining the TT group with functionalised aromatic or unsaturated comonomers can further improve the solubility and the charge transport properties. Variation of the aromatic groups provides a method of tailoring the band gap of the compounds. This leads to better stability and higher charge carrier mobility.

Especially preferred are compounds wherein the TT group is substituted by two alkyl or fluoroalkyl groups. The introduction of fluoroalkyl and alkyl side chains into the TT group improves their solubility and therefore their solution processibility. Furthermore, the presence of fluoroalkyl side chains also renders these materials effective as n-type semiconductors. The electron-withdrawing nature of the fluoroalkyl substituents will also lower the HOMO further and result in a more stable material, which is less susceptible to oxidation.

Particularly preferred are compounds of formula I

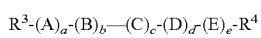

wherein

A, B, C, D and E are independently of each other a group of formula II

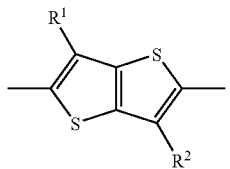

or denote —CX$^1$═CX$^2$—, —C≡C— or an arylene or heteroarylene group that is optionally substituted with one or more groups R$^1$ wherein at least one of A, B, C, D and E is a group of formula II, R$^1$ and R$^2$ independently of each other denote H, halogen, aryl or heteroaryl which are optionally substituted, P-Sp-, P*-Sp-, or straight chain, branched or cyclic alkyl with 1 to 20 C-atoms, which may be unsubstituted, mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —O—CO—O—, —S—CO—, —CO—S—, —CX$^1$═CX$^2$— or —C≡C— in such a manner that O and/or S atoms are not linked directly to one another, R$^3$ and R$^4$ are independently of each other P-Sp-, P*-Sp- or have one of the meanings of R$^1$, with at least one of R$^3$ and R$^4$ being P-Sp- or P*-Sp-, X$^1$ and X$^2$ are independently of each other H, F, Cl or CN, P is a polymerisable or reactive group, P* is a group that can be converted into or substituted by a polymerisable or reactive group P, or a protected form of group P, Sp is a spacer group or a single bond, R$^0$, R$^{00}$ and R$^{000}$ are independently of each other H, alkyl with 1 to 12 C-atoms or aryl, a, b, c and d are independently of each other 0, 1, 2 or 3, with a+b+c+d>0.

R$^3$ and R$^4$ are hereinafter also referred to as "terminal groups".

Especially preferred compounds of formula I wherein R$^1$ and R$^2$ are identical groups.

Further preferred are compounds of formula I that are mesogenic or liquid crystalline, in particular those having a smectic and/or nematic phase.

Further preferred are compounds of formula I wherein

A, B, C, D and E are different from substituted or unsubstituted thieno[2,3-b]thiophene-2,5-diyl, at least one of A, B, C, D and E is phenylene-1,4-diyl, thiophene-2,5-diyl, selenophene-2,5-diyl or naphthalene-2,6-diyl that is optionally substituted by one or two groups R$^1$ different from H, R$^1$ and R$^2$ are H, R$^1$ and/or R$^2$ are selected from C$_1$-C$_{20}$-alkyl that is optionally substituted with one or more fluorine atoms, C$_1$-C$_{20}$-alkenyl, C$_1$-C$_{20}$-alkynyl, C$_1$-C$_{20}$-ester, C$_1$-C$_{20}$-amino, C$_1$-C$_{20}$-fluoroalkyl, and optionally substituted aryl or heteroaryl, very preferably C$_1$-C$_{20}$-alkyl or C$_1$-C$_{20}$-fluoroalkyl, R$^3$ and R$^4$ are P-Sp- or P*-Sp-, P* is —OH or —O—Si—R$^0$R$^{00}$R$^{000}$, preferably wherein R$^0$, R$^{00}$ and R$^{000}$ are identical or different groups selected from aryl or C$_{1-12}$-alkyl, preferably C$_1$-C$_6$-alkyl, like methyl, ethyl, isopropyl, tert-butyl or phenyl the compounds comprise one, two or three TT groups, the compounds comprise one, two or three TT groups and one, two, three or four groups selected from phenylene-1,4-diyl, thiophene-2,5-diyl, selenophene-2,5-diyl and naphthalene-2,6-diyl wherein all of these groups are optionally substituted by one or two groups R$^1$ different from H.

If one of A, B, C, D and E is arylene or heteroarylene, it is preferably a mono-, bi- or tricyclic aromatic or heteroaromatic group with up to 25 C atoms, wherein the rings can be fused, and in which the heteroaromatic group contains at least one hetero ring atom, preferably selected from N, O and S. It is optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—, —CH═CH— or —C≡C— in such a manner that O and/or S atoms are not linked directly to one another.

Preferred arylene or heteroarylene groups are selected from phenylene in which, in addition, one or more CH groups may be replaced by N, or naphthalene, alkyl fluorene or oxazole, thiophene, selenophene, dithienothiophene, wherein all these groups are optionally mono- or polysubstituted with L as defined above.

Especially preferred arylene or heteroarylene groups are 1,4-phenylene, fluorinated 1,4-phenylene, 2,5-pyridine, 2,5-pyrimidine, p,p'-biphenyl, naphthalene-2,6-diyl, thiophene-2,5-diyl, selenophene-2,5-diyl, fluorinated or alkylated thiophene-2,5-diyl or selenophene-2,5-diyl, 2,2'-dithiophene, fluorinated or alkylated 2,2'-dithiophene, fluorinated benzo[1,2-b:4,5-b']dithiophene, 2,5-thiazole, 2,5-thiadiazole, 2,5-oxazole and 2,5-oxadiazole, all of which are unsubstituted, mono- or polysubstituted with L as defined above.

If one of R$^{1-4}$ is aryl or heteroaryl, it is preferably a mono-, bi- or tricyclic aromatic or heteroaromatic group with up to 25 C atoms, wherein the rings can be fused, and in which the heteroaromatic group contains at least one hetero ring atom, preferably selected from N, O and S. It is optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—, —CH═CH— or —C≡C— in such a manner that O and/or S atoms are not linked directly to one another.

Especially preferred aryl and heteroaryl groups are phenyl, fluorinated phenyl, pyridine, pyrimidine, biphenyl, naphthalene, thiophene, selenophene, fluorinated thiophene, benzo[1,2-b:4,5-b']dithiophene, thiazole and oxazole, all of which are unsubstituted, mono- or polysubstituted with L as defined above.

If one of R$^{1-4}$ is an alkyl or alkoxy radical, i.e. where the terminal CH$_2$ group is replaced by —O—, this may be straight-chain or branched. It is preferably straight-chain, has 3 to 8 carbon atoms and accordingly is preferably propyl, butyl, pentyl, hexyl, heptyl, octyl, propoxy, butoxy, pentoxy, hexyloxy, heptoxy, or octoxy, furthermore nonyl, decyl, undecyl, dodecyl, tridecyl, tetradecyl, pentadecyl, nonoxy, decoxy, undecoxy, dodecoxy, tridecoxy or tetradecoxy, for example.

Fluoroalkyl or fluorinated alkyl or alkoxy is preferably straight chain $(O)C_iF_{2i+1}$, wherein i is an integer from 1 to 20, in particular from 3 to 15, very preferably $(O)C_3F_7$, $(O)C_4F_9$, $(O)C_5F_{11}$, $(O)C_6F_{13}$, $(O)C_7F_{15}$ or $(O)C_8F_{17}$, most preferably $(O)C_6F_{13}$.

$CX^1=CX^2$ is preferably —CH=CH—, —CH=CF—, —CF=CH—, —CF=CF—, —CH=C(CN)— or —C(CN)=CH—.

Halogen is preferably F, Br or Cl.

Hetero atoms are preferably selected from N, O and S.

The reactive or polymerisable group P is a group that is capable of participating in a polymerisation reaction, like radicalic or ionic chain polymerisation, polyaddition or polycondensation, or capable of being grafted, for example by condensation or addition, to a polymer backbone in a polymeranalogous reaction. Especially preferred are polymerisable groups for chain polymerisation reactions, like radicalic, cationic or anionic polymerisation. Very preferred are polymerisable groups comprising a C—C double or triple bond, and polymerisable groups capable of polymerisation by a ring-opening reaction, like oxetanes or epoxides.

Very preferably the polymerisable or reactive group P is selected from $CH_2=CW^1$—COO—, $CH_2=CW^1$—CO—,

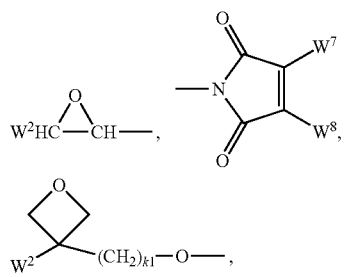

$CH_2=CW^2$—$(O)_{k1}$—, $CH_3$—CH=CH—O—, $(CH_2=CH)_2$ CH—OCO—, $(CH_2=CH$—$CH_2)_2$CH—OCO—, $(CH_2=CH)_2$CH—O—, $(CH_2=CH$—$CH_2)_2$N—, $(CH_2=CH$—$CH_2)_2$N—CO—, HO—$CW^2W^3$—, HS—$CW^2W^3$—, $HW^2$N—, HO—$CW^2W^3$—NH—, $CH_2=CW^1$—CO—NH—, $CH_2=CH$—$(COO)_{k1}$-Phe-$(O)_{k2}$—, $CH_2=CH$—$(CO)_{k1}$-Phe-$(O)_{k2}$—, Phe-CH=CH—, HOOC—, OCN—, and $W^4W^5W^6Si$—, with $W^1$ being H, Cl, CN, $CF_3$, phenyl or alkyl with 1 to 5 C-atoms, in particular H, Cl or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, and $k_1$ and $k_2$ being independently of each other 0 or 1.

Especially preferred groups P are $CH_2=CH$—COO—, $CH_2=C(CH_3)$—COO—, $CH_2=CH$—, $CH_2=CH$—O—, $(CH_2=CH)_2$CH—OCO—, $(CH_2=CH)_2$CH—

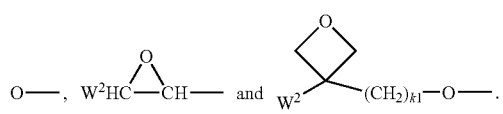

Very preferred are acrylate and oxetane groups. Oxetanes produce less shrinkage upon polymerization (cross-linking), which results in less stress development within films, leading to higher retention of ordering and fewer defects. Oxetane cross-linking also requires a cationic initiator, which unlike free radical initiator is inert to oxygen.

As spacer group Sp all groups can be used that are known for this purpose to the skilled in the art. The spacer group Sp is preferably of formula Sp'-X, such that P-Sp- is P-Sp'-X— and P*-Sp- is P*-Sp'-X—, wherein Sp' is alkylene with up to 20 C atoms which may be unsubstituted, mono- or poly-substituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, X is —O—, —S—, —CO—, —COO—, —OCO—, —O—COO—, —CO—$NR^0$—, —$NR^0$—CO—, —$NR^0$—CO—$NR^{00}$—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^0$—, —$CX^1=CX^2$—, —C≡C—, —CH=CH—COO—, —OCO—CH=CH— or a single bond, and $R^0$, $R^{00}$, $X^1$ and $X^2$ have one of the meanings given above.

X is preferably —O—, —S—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CX^1=CX^2$—, —C≡C— or a single bond, in particular —O—, —S—, —C≡C—, —$CX^1=CX^2$— or a single bond, very preferably a group that is able to from a conjugated system, such as —C≡C— or —$CX^1=CX^2$—, or a single bond.

Typical groups Sp' are, for example, —$(CH_2)_p$—, —$(CH_2CH_2O)_q$—$CH_2CH_2$—, —$CH_2CH_2$—S—$CH_2CH_2$— or —$CH_2CH_2$—NH—$CH_2CH_2$— or —$(SiR^0R^{00}$—$O)_p$—, with p being an integer from 2 to 12, q being an integer from 1 to 3 and $R^0$ and $R^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Further preferred are compounds with one or two groups P-Sp- or P*-Sp- wherein Sp is a single bond.

In case of compounds with two groups P-Sp or P*-Sp-, respectively, each of the groups P or P* and the spacer groups Sp can be identical or different.

Another preferred embodiment relates to compounds comprising one or more groups P*-Sp-, wherein P* is a group that can be converted to or substituted by a polymerisable or reactive group P as defined above. Preferably P* is a group that is less reactive than P, for example towards spontaneous polymerisation. These compounds can be used for example as intermediates in the synthesis of polymerisable compounds of formula I having one or more groups P, or as a precursor material for polymerisable compounds which are too reactive to be stored or transported for longer periods of time. The group P* is preferably chosen such that it can easily be transformed into or substituted by a group P by known methods. For example, it can be a protected form of group P. Preferred groups P* are for example —OH or silyl groups like —O—Si—$R^0R^{00}R^{000}$, for example —O—$Si(CH_3)_3$, —O—Si-(isopropyl)$_3$, —O—Si-(phenyl)$_3$, —O—Si—(CH$_3$)$_2$(phenyl), —O—Si(CH$_3$)$_2$(tert-butyl) or the like, which can be reacted e.g. into polymerisable (meth)acrylate end groups.

Further preferred are compounds selected from the following formulae

R$^3$-TT-(B)$_b$-TT-R$^4$      I-1

R$^3$-(A)$_a$-TT-(C)$_c$—R$^4$      I-2 wherein TT is a group of formula II and R$^3$, R$^4$, A, B, C, a, b and c are as defined above. Very preferred are compounds of formulae I-1 and I-2 wherein a, b and c are 1 or 2, furthermore those wherein A, B and C are selected from phenylene-1,4-diyl, thiophene-2,5-diyl, selenophene-2,5-diyl and naphthalene-2,6-diyl, or B is TT, wherein all of these groups are optionally substituted by one or two groups R$^1$ different from H.

Especially preferred are compounds selected from the following formulae

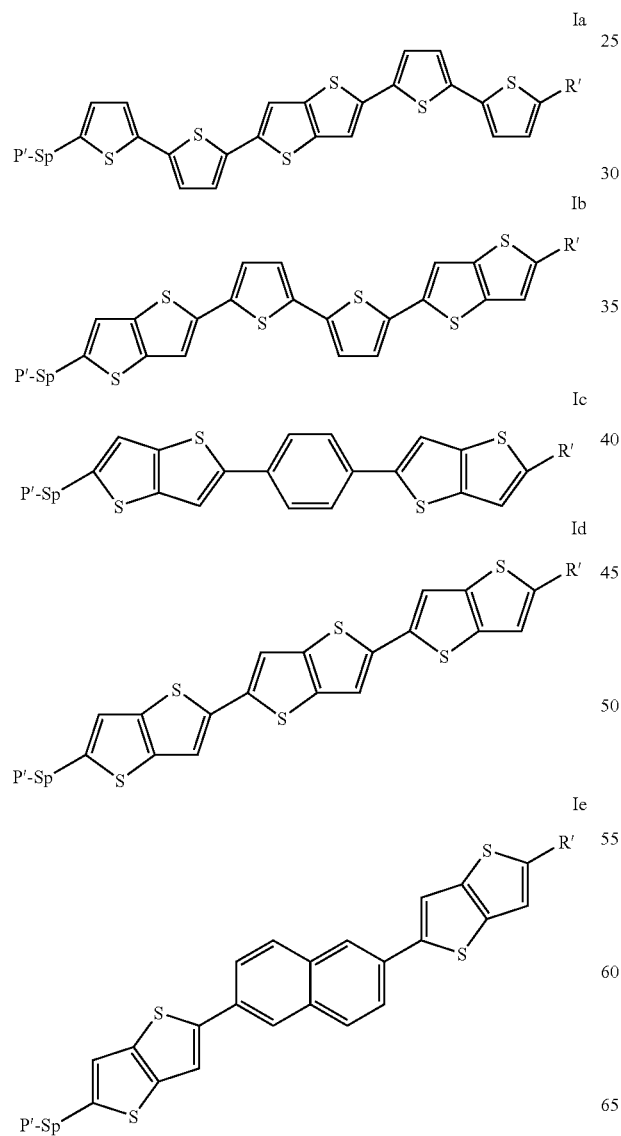

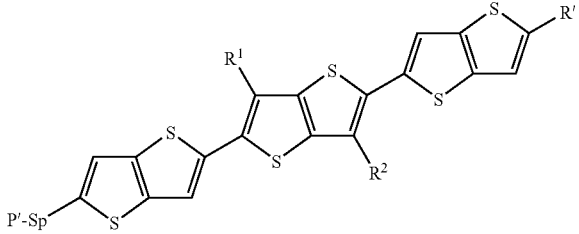

wherein Sp, R$^1$ and R$^2$ are as defined in formula I, P' is P or P* as defined in formula I, and R' has one of the meanings of R$^3$ given in formula I.

The compounds of the present invention can be synthesized according to or in analogy to known methods or to the methods described below. Further methods can be taken from the examples.

Part A

Synthesis of 3,6-dialkyl-thieno[3,2-b]thiophene

With the exception of 3,6-dimethyl, the preparation of 3,6-dialkylated TTs has not been reported in prior art. A one-pot procedure to 3,6-dimethylated thieno[3,2-b]thiophene as shown in Scheme 1 below has been reported by Nakayama et al., Heterocycles 1994, 38, p143. However, this method has the disadvantage that it is not amenable to the preparation of longer chain alkyl derivatives, due the mechanism of ring closure. The incorporation of longer alkyl chains is desired to improve the solubility and liquid crystalline behaviour of the molecules.

Scheme 1: Preparation of dimethyl-thieno[3,2-b]thiophene (prior art)

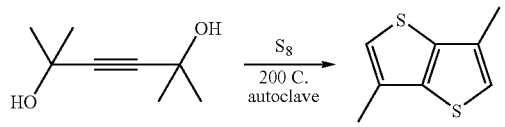

The synthesis of thieno[3,2-b]thiophene (1) (R═H) as depicted in Scheme 2 has been reported in Fuller et al., J. Chem. Soc. Perkin Trans. 1997, 1, 3465-70. The same reference also reports a procedure for the preparation of 3,6-dibromothieno[3,2-b]thiophene (2), via tetrabromination and reduction of the thieno[3,2-b]thiophene core as shown in Scheme 3. The dibromo intermediate (2) was converted into thioalkyl (—SR) derivatives via lithiation and subsequent reaction with electrophilic disulfides. However, thioethers are undesired in the present case because the electron rich nature of these side chains affords polymers that are oxidatively unstable. Moreover long chain alkyl derivatives could not be incorporated by an analogous route due to the low reactivity of alkyl halides which prevented reaction at low temperature. At temperatures greater than −78° C. the di-lithium salt of (2) ring opens (see Fuller et al J. Chem. Soc. Perkin Trans. 1999, 1, p 1273) to afford non-fused products.

Scheme 2: Synthesis of thieno-[3,2-b]thiophene (prior art)

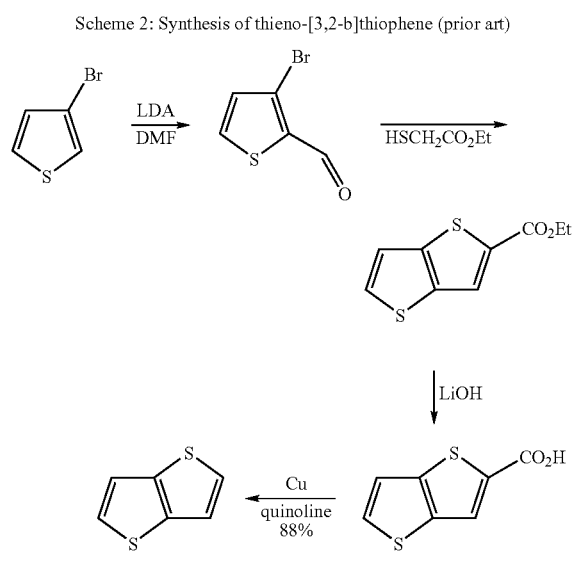

Scheme 3: Preparation of 3,6-dialkylthienothiophene via dibromo intermediate (prior art)

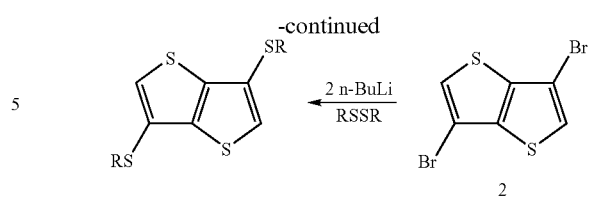

A preferred synthesis of 3,6-dialkylthieno[3,2-b] thiophene according to the present invention is exemplarily described in scheme 4, utilising dibromo intermediate (2). Cross coupling of (2) with organozinc reagents in the presence of a bidentate palladium catalyst (such as Pd(dppf)Cl$_2$) was found to occur in excellent yields under microwave heating. Thus heating propylzinc bromide, 3,6-dibromothieno[3,2-b]thiophene and Pd(dppf)Cl$_2$ in THF at 140° C. for 7 min afforded a 93% yield of 3,6-dipropylthieno[3,2-b]thiophene.

Scheme 4

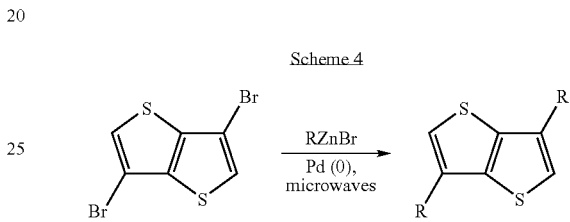

As outlined in schemes 5-7 compounds of formula I can be synthesised by transition metal catalysed cross-coupling methodologies. A convenient procedure is the Suzuki reaction involving aryl boronic acids or esters, however the present compounds can also be synthesised by the transition metal catalysed coupling of organotins (Stille reaction), organozincs (Negishi coupling), organomagnesiums (Kumada coupling), organosilicon reagents or aryl lithiums. The polymerisable endgroups can be introduced before the cross-coupling step (for example see scheme 7), or afterwards as shown in scheme 5.

Scheme 5

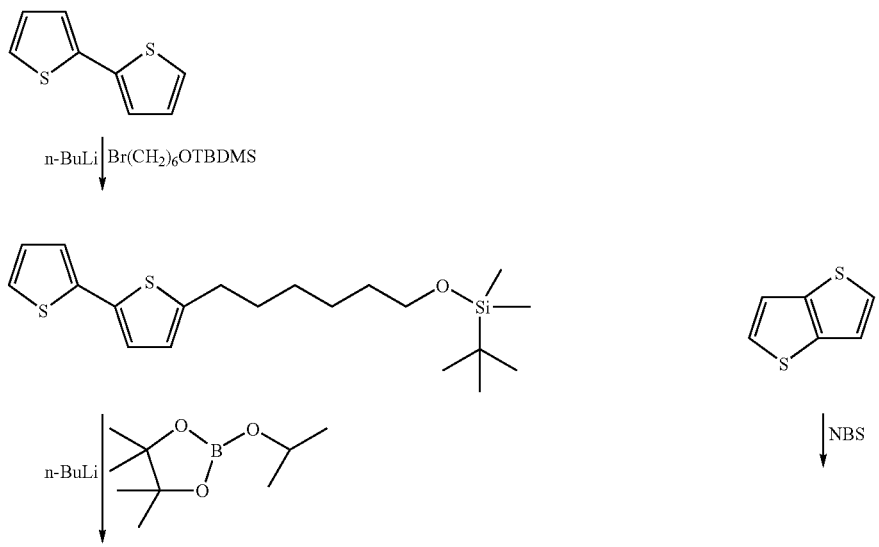

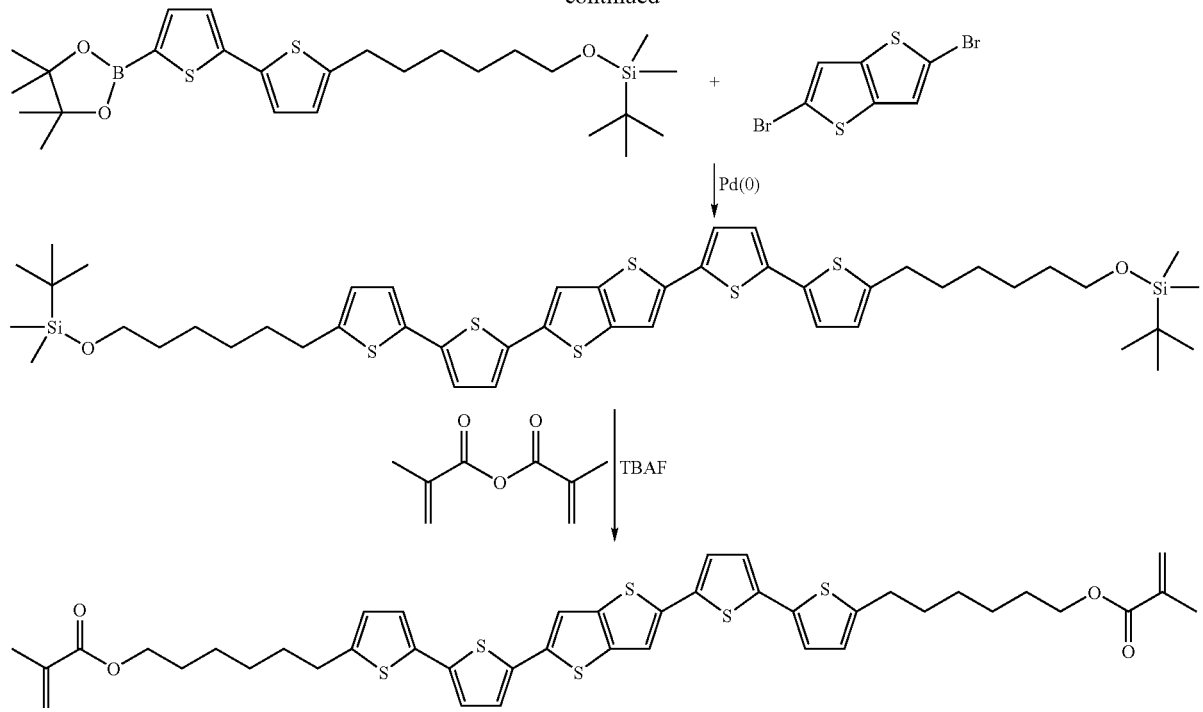

Compounds containing a thieno[3,2-b]thiophene in the central portion of the molecule (formula I-2) are readily synthesised by the palladium catalysed Suzuki reaction between 2,5-dibromothieno[3,2-b]thiophene, itself prepared by the bromination of thieno[3,2-b]thiophene, and a boronic ester (scheme 5). The resulting compound containing silyl protecting groups is readily converted into the desired methacrylate containing compound by treatment with a fluoride source and methacrylic anhydride or methacryloyl chloride.

Scheme 6

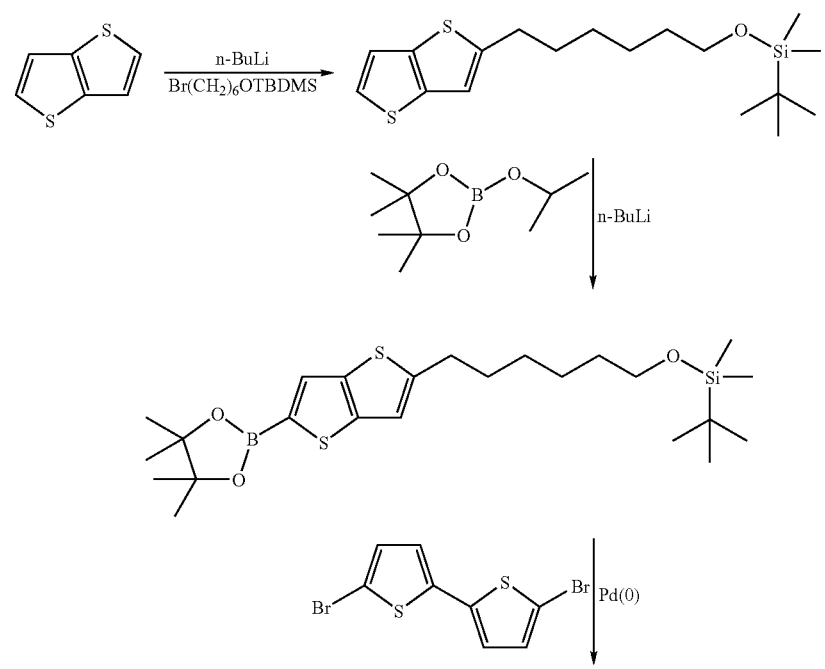

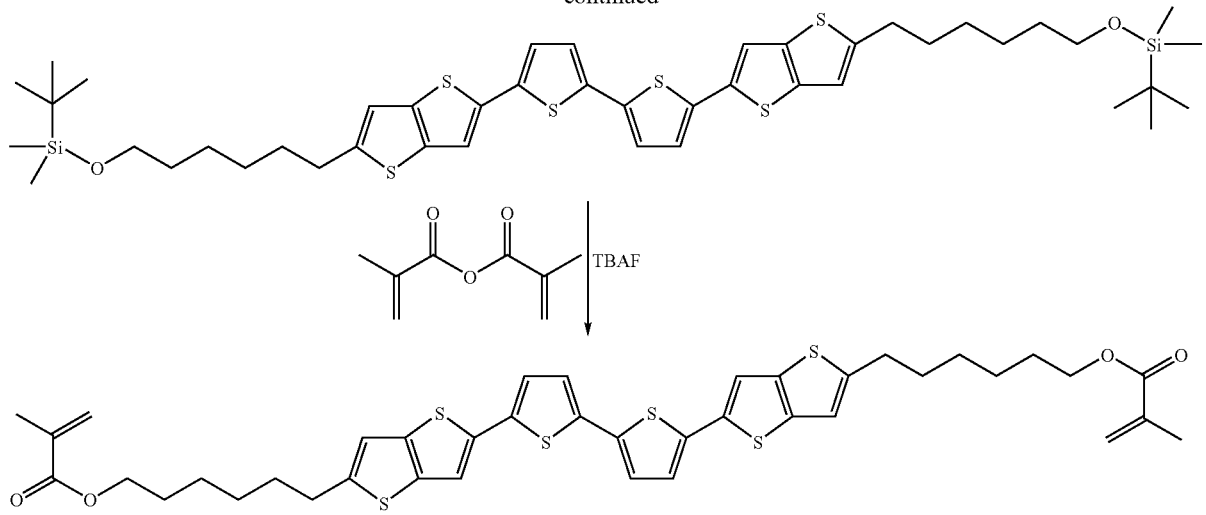

Compounds containing thieno[3,2-b]thiophene's in the outer portions of the molecule (formula I-1) are readily synthesised by the palladium catalysed Suzuki reaction between a thieno[3,2-b]thiophene boronic ester and an aromatic dibromide (scheme 6). Thieno[3,2-b]thiophene was therefore mono-lithiated with one equivalent of n-butyllithium and subsequently reacted with a protected bromoalcohol. The resulting product was lithiated again and reacted with 2-isopropoxy-4,4,5,5-tetramethyl-1,3,2-dioxaborolane to afford the resulting boronic ester. This was readily coupled with 5,5'-dibromo-2,2'-bithiophene to afford the silyl protected mesogen, which was converted to the methacrylate by the methods described above.

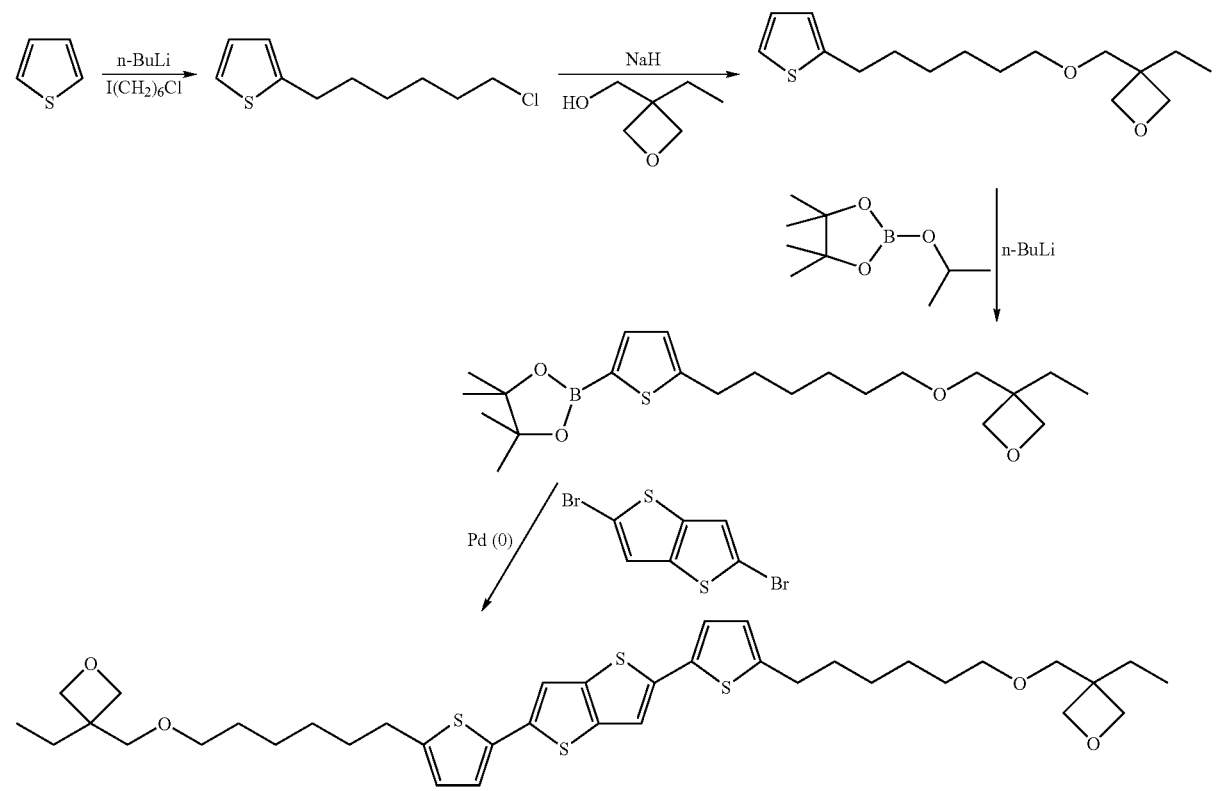

Scheme 7

The reactive endgroup can also be introduced to the molecule during the Suzuki cross-coupling reaction (scheme 7). In this example a thiophene boronic ester containing a reactive oxetane group is cross-coupled with 2,5-dibromothieno[3,2-b]thiophene to afford the target molecule directly. The oxetane group is readily introduced by reaction of 3-ethyl-3-oxetanemethanol with a chloroalkyl-thiophene. Subsequent lithiation of the thiophene with n-butyl lithium followed by reaction with 2-isoproxy-4,4,5,5-tetramethyl-1,3,2-dioxaborolane affords the boronic ester.

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g., from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantation of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns or tracts in electronic applications such as printed circuit boards and condensers.

A preferred embodiment of the present invention relates to compounds of formula I and its preferred subformulae that are mesogenic or liquid crystalline.

These materials are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid crystal state can be fixed by in situ polymerisation or crosslinking via the groups P to yield polymer films with high charge carrier mobility and high thermal, mechanical and chemical stability.

For example, a device can be made from a polymerisable liquid crystal material by polymerisation in situ, wherein the liquid crystal material comprises one or more monomers of formula I and its preferred subformulae. Alternatively the liquid crystal polymer is prepared first from a liquid crystal material comprising one or more monomers of formula I and its preferred subformulae, for example by polymerisation in solution, and the isolated polymer is then used to make the device.

It is also possible to copolymerise the monomers according to the present invention with other polymerisable mesogenic or liquid crystal monomers that are known from prior art, in order to induce or enhance liquid crystal phase behaviour.

Thus, another aspect of the invention relates to a polymerisable liquid crystal material comprising one or more monomers of the present invention as described above and below comprising at least one polymerisable group, and optionally comprising one or more further polymerisable compounds, wherein at least one of the polymerisable monomers of the present invention and/or the further polymerisable compounds is mesogenic or liquid crystalline.

Particularly preferred are liquid crystal materials having a nematic and/or smectic phase. For FET applications smectic materials are especially preferred. For OLED applications nematic or smectic materials are especially preferred.

Another aspect of the present invention relates to an anisotropic polymer film with charge transport properties obtainable from a polymerisable liquid crystal material as defined above that is aligned in its liquid crystal phase into macroscopically uniform orientation and polymerised or crosslinked to fix the oriented state.

Preferably polymerisation is carried out as in-situ polymerisation of a coated layer of the material, preferably during fabrication of the electronic or optical device comprising the inventive semiconductor material. In case of liquid crystal materials, these are preferably aligned in their liquid crystal state into homeotropic orientation prior to polymerisation, where the conjugated pi-electron systems are orthogonal to the direction of charge transport. This ensures that the intermolecular distances are minimised and hence then energy required to transport charge between molecules is minimised. The molecules are then polymerised or crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45-66.

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by I. Sage in "Thermotropic Liquid Crystals", edited by G. W. Gray, John Wiley & Sons, 1987, pages 75-77, and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Monomers according to the present invention can also be copolymerised with polymerisable mesogenic compounds to induce or enhance liquid crystal phase behaviour. Polymerisable mesogenic compounds that are suitable as comonomers are known in prior art and disclosed for example in WO 93/22397; EP 0,261,712; DE 195,04,224; WO 95/22586 and WO 97/00600.

Another aspect of the invention relates to a liquid crystal side chain polymer (SCLCP) obtained from a polymerisable liquid crystal material as defined above by polymerisation or polymeranaloguous reaction. Particularly preferred are SCLCPs obtained from one or more monomers of formula I and its preferred subformulae wherein one or both, preferably one, of the terminal groups denotes a polymerisable or reactive group, or from a polymerisable mixture comprising one or more of said monomers.

Another aspect of the invention relates to an SCLCP obtained from one or more monomers of formula I and its preferred subformulae wherein one or both of the terminal groups are a polymerisable group, or from a polymerisable liquid crystal mixture as defined above, by copolymerisation or polymeranaloguous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically <4 Å) pi-pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

SCLCPs can be prepared from the polymerisable compounds or mixtures according to the invention by the methods described above, or by conventional polymerisation techniques which are known to those skilled in the art, including for example radicalic, anionic or cationic chain polymerisation, polyaddition or polycondensation. Polymerisation can be carried out for example as polymerisation in solution, without the need of coating and prior alignment, or polymerisation in situ. It is also possible to form SCLCPs by grafting compounds according to the invention with a suitable reactive group, or mixtures thereof, to presynthesized isotropic or anisotropic polymer backbones in a polymeranaloguous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added, e.g., to polysiloxane backbones with Si—H groups. It is also possible to form SCLCPs by copolymerisation or polymeranaloguous reaction from the inventive compounds together with conventional mesogenic or non mesogenic comonomers. Suitable comonomers are known to those skilled in the art. In principle it is possible to use all conventional comonomers known in the art that carry a reactive or polymerisable group capable of undergoing the desired polymer-forming reaction, like for example a polymerisable or reactive group P as defined above. Typical mesogenic comonomers are for example those mentioned in WO 93/22397, EP 0 261 712, DE 195 04 224, WO 95/22586, WO 97/00600 and GB 2 351 734. Typical non mesogenic comonomers are for example alkyl acrylates or alkyl methacrylates with alkyl groups of 1 to 20 C atoms, like methyl acrylate or methyl methacrylate.

SCLCPs obtained from the inventive compounds or mixtures by polymerisation or copolymerisation have a backbone that is formed by the polymerisable group P.

The compounds of the present invention are useful as optical, electronic and semiconductor materials, in particular as charge transport materials in field effect transistors (FETs), e.g., as components of integrated circuitry, ID tags or TFT applications. Alternatively, they may be used in organic light emitting diodes (OLEDs) in electroluminescent display applications or as backlight of, e.g., liquid crystal displays, as photovoltaics or sensor materials, for electrophotographic recording, and for other semiconductor applications.

Monomers according to the invention show advantageous solubility properties which allow production processes using solutions of these compounds. Thus films, including layers and coatings, may be generated by low cost production techniques, e.g., spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known, e.g., from U.S. Pat. No. 5,892,244, WO 00/79617, U.S. Pat. No. 5,998,804, and from the references cited in the background and prior art chapter and listed below. Due to the advantages, like low cost production using the solubility properties of the compounds according to the invention and thus the processability of large surfaces, preferred applications of these FETs are such as integrated circuitry, TFT-displays and security applications.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with monetry value, like stamps, tickets, shares, cheques etc.

Alternatively, the materials according to the invention may be used in organic light emitting devices or diodes (OLEDs), e.g., in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable compounds or materials for the use in OLEDs is generally known by a person skilled in the art, see, e.g., Meerholz, Synthetic Materials, 111-112, 2000, 31-34, Alcala, J. Appl. Phys., 88, 2000, 7124-7128 and the literature cited therein.

According to another use, the inventive compounds, materials or films, especially those which show photoluminescent properties, may be employed as materials of light sources, e.g., of display devices such as described in EP 0 889 350 A1 or by C. Weder et al., Science, 279, 1998, 835-837.

According to another use, the inventive compounds, materials or films can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913.

The examples below serve to illustrate the invention without limiting it. In the foregoing and the following, all temperatures are given in degrees Celsius, and all percentages are by weight, unless stated otherwise. All reactions were run under nitrogen atmosphere unless otherwise noted. The following abbreviations are used to illustrate the liquid crystalline phase behaviour of the compounds: G=glass transition; K=crystalline; N=nematic; S=smectic; Ch=cholesteric; I=isotropic. The numbers between the symbols indicate the phase transition temperatures in ° C. Phase transitions were determined by a mixture of DSC and optical microscopy. $S_x$ and $S_{x1}$ refer to smectic transitions of undetermined nature.

EXAMPLE 1

Compound 1 is prepared as outlined below:

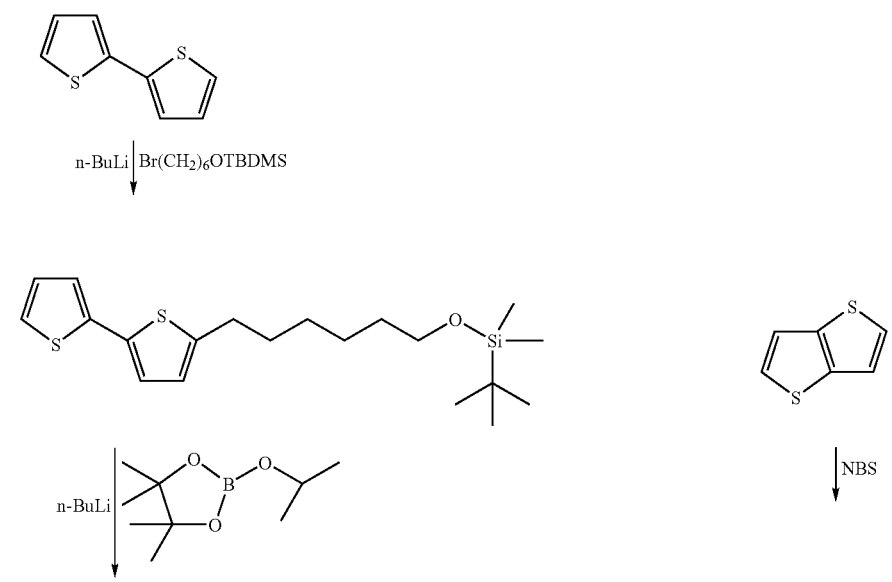

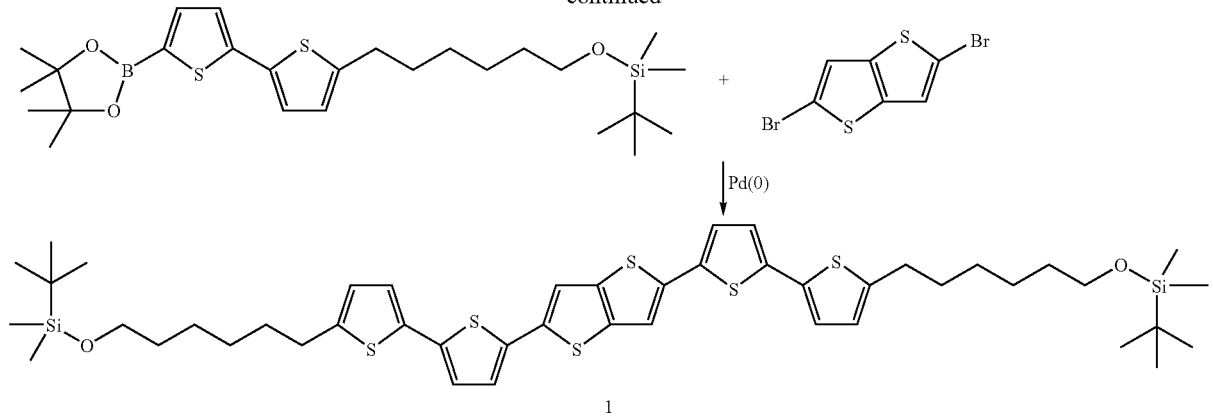

(6-[2,2']Bithiophenyl-5-yl-hexyloxy)-tert-butyl-dimethylsilane

To a stirred solution of 2,2'-bithiophene (10.0 g, 60.24 mmol) in dry THF (150 ml) was added n-butyllithium (2.5 M in hexanes, 20.0 ml, 50.0 mmol) dropwise at −78° C. under nitrogen. After complete addition, the mixture was allowed to warm to room temperature, with stirring, over 2 h, followed by the addition of 6-bromohexyloxy-tert-butyldimethylsilane (14.75 g, 50.0 mmol). The resultant mixture was stirred overnight at room temperature. The reaction was quenched with sat. aq. ammonium chloride, and the reaction mixture was extracted with ethyl acetate (3×70 ml). The combined organic extracts were washed with water, brine, and dried over magnesium sulphate. The solvent was removed under reduced pressure and the residue was chromatographyed (silica gel, petroleum/ethyl acetate from 100:0 to 20:1), to afford the product as a pale green oil (15.07 g, 79%). $^1$H NMR (300 MHz, CDCl$_3$): δ (ppm) 7.08 (m, 1H, Ar—H), 7.03 (m, 1H, Ar—H), 6.92 (m, 2H, Ar—H), 6.61 (d, J=3.6 Hz, 1H, Ar—H), 3.55 (t, J=6.2 Hz, 2H, OCH$_2$), 3.34 (t, J=6.8 Hz, 2H, ArCH$_2$), 1.25-1.85 (m, 8H, CH$_2$), 0.86 (s, 9H, CH$_3$), 0.01 (s, 6H, CH$_3$); $^{13}$C NMR (75 MHz, CDCl$_3$): δ (ppm) 145.1 (quat.), 138.0 (quat.), 134.8 (quat.), 127.6 (CH), 124.7 (CH), 123.7 (CH), 123.4 (CH), 122.9 (CH), 63.0 (OCH$_2$), 33.8 (CH$_2$), 32.9 (CH$_2$), 32.7 (CH$_2$), 28.0 (CH$_2$), 26.0 (CH$_3$) 25.1 (CH$_2$), 18.4 (quat.), −5.2 (CH$_3$); MS (m/e): 380 (M$^+$, 27%), 323 (63), 179 (100), 75 (37).

2-{5'-[6-(tert-Butyl-dimethyl-silanyloxy)-hexyl]-[2,2']bithiophenyl-5-yl}-4,4,5,5-tetramethyl-[1,3,2]dioxaborolane To an ice-cooled solution of (6-[2,2']bithiophenyl-5-yl-hexyloxy)-tert-butyl-dimethylsilane (10 g, 19.76 mmol) in anhydrous THF (150 ml) was added dropwise a solution of n-butyllithium (2.5 M in hexanes, 7.91 ml, 19.76 mmol) under nitrogen, with stirring. After 2 h, pinacol boronate (4.04 g, 21.72 mmol) was added. The ice bath was removed, and the resultant mixture was stirred overnight at room temperature. The reaction was quenched with the addition of saturated aqueous NH$_4$Cl and the mixture extracted with ethyl acetate (3×70 ml). The combined organic extracts were washed with brine, dried over magnesium sulphate, and evaporated under reduced pressure. The residue was purified by column chromatography on silica, eluting with petroleum ether/ethyl (9:1), to give the product as a blue oil (9.52 g, 72%). $^1$H NMR (300 MHz, CDCl$_3$): δ (ppm) 7.46 (d, J=3.6 Hz, 1H, Ar—H), 7.10 (d, J=3.6 Hz, 1H, Ar—H), 6.99 (d, J=3.4 Hz, 1H, Ar—H), 6.62 (d, J=3.4 Hz, 1H, Ar—H), 3.56 (t, J=6.4 Hz, 2H, OCH$_2$), 2.73 (t, J=7.4 Hz, 2H, ArCH$_2$), 1.21-1.70 (m, 20H, CH$_2$ and CH$_3$), 0.86 (s, 9H, CH$_3$), 0.01 (s, 6H, CH$_3$); $^{13}$C NMR (75 MHz, CDCl$_3$): δ (ppm) 145.9 (2×quat.), 144.8 (quat.), 138.0 (CH.), 134.7 (quat.), 125.0 (CH), 124.2 (CH), 124.1 (CH), 84.1 (quat.), 63.2 (OCH$_2$), 32.8 (CH$_2$), 31.6 (CH$_2$), 30.2 (CH$_2$), 28.9 (CH$_2$), 26.0 (CH$_3$) 25.6 (CH$_2$), 24.8 (CH$_3$), 18.4 (quat.), −5.2 (CH$_3$); MS (m/e): 506 (M$^+$, 32%), 331 (31), 305 (31), 279 (100), 261 (32), 205 (51), 83 (71).

2,5-Dibromo-thieno[3,2-b]thiophene

N-bromosuccinimide (1.24 g, 6.94 mmol) was added to a solution of thieno[3,2-b]thiophene (1.0 g, 6.94 mmol) in DMF (30 ml) at room temperature and this mixture was stirred for 3 h. After this water (100 ml) was added and the precipitate formed was filtrated off, washed with water and dried to give 2 as a white solid (1.87 g, 88%). $^1$H NMR (300 MHz, CDCl$_3$): δ (ppm) 7.14 (s, 2H, Ar—H); $^{13}$C NMR (75 MHz, CDCl$_3$): δ (ppm) 138.3 (quat.), 121.8 (CH), 113.7 (quat.).

2,5-Bis-{5'[6-(tert-butyldimethylsilanyloxy)-hexyl]-[2,2']bithiophenyl-5-yl}-thieno[3,2-b]thiophene (1)

Tetrakis(triphenylphosphine)palladium(0) (0.05 g) was added to a solution 2,5-dibromothieno[3,2-b]thiophene (0.10 g, 0.34 mmol) in dry THF (30 ml), with stirring, under nitrogen. After 20 min, 2-{5'-[6-(tert-butyl-dimethyl-silanyloxy)-hexyl]-[2,2']bithiophenyl-5-yl}-4,4,5,5-tetramethyl-[1,3,2]dioxaborolane (0.51 g, 1.01 mmol) and a solution of potassium carbonate (0.28 g, 2.03 mmol) in water (10 ml) were added. The resultant mixture was heated at reflux for 1.5 h. After cooling, water (100 ml) was added and the precipitate filtered off, washed with water and diethyl ether, to give a yellow solid, which was recrystallised with toluene to offer yellow crystals (0.17 g, 57%).

LC phases: K-158° C.-S$_X$-182° C.-S$_{X1}$-243° C.-I.

Elementary Analysis Found: C, 61.0; H, 6.8; S, 20.7. C$_{46}$H$_{64}$O$_2$S$_6$Si$_2$ requires C, 61.5; H, 7.2; S, 21.3%. $^1$H NMR (300 MHz, CDCl$_3$): δ (ppm) 7.09 (d, J=3.7 Hz, 2H, Ar—H), 7.01 (m, 6H, Ar—H), 6.69 (d, J=3.4 Hz, 2H, Ar—H), 3.60 (t, J=6.5 Hz, 4H, OCH$_2$), 2.80 (t, J=7.3 Hz, 4H, ArCH$_2$), 1.31-1.84 (m, 16H, CH$_2$), 0.90 (s, 18H, CH$_3$), 0.05 (s, 12H, CH$_3$); $^{13}$C NMR (75 MHz, CDCl$_3$): δ (ppm) 145.8 (quat.), 138.8

(quat.), 138.4 (quat.), 137.2 (quat.), 134.3 (quat.), 128.0 (quat.), 125.0 (CH), 124.5 (CH), 123.63 (CH), 123.58 (CH), 115.5 (CH), 63.2 (OCH$_2$), 32.8 (CH$_2$), 31.6 (CH$_2$), 30.2 (CH$_2$), 28.9 (CH$_2$), 26.0 (CH$_3$) 25.6 (CH$_2$), 18.4 (quat.), −5.2 (CH$_3$).

EXAMPLE 2

Compound 2 is prepared as outlined below:

Hz, 1H, Ar—H), 7.15 (d, J=5.2 Hz, 1H, Ar—H), 6.93 (s, 1H, Ar—H), 3.60 (t, J=6.4 Hz, 2H, OCH$_2$), 2.86 (t, J=7.9 Hz, 2H, ArCH$_2$), 1.35-1.90 (m, 8H, CH$_2$), 0.90 (s, 9H, CH$_3$), 0.05 (s, 6H, CH$_3$); $^{13}$C NMR (75 MHz, CDCl$_3$): δ (ppm) 148.4 (quat.), 138.7 (quat.), 137.4 (quat.), 125.3 (CH), 119.4 (CH), 116.2 (CH), 63.2 (OCH$_2$), 32.8 (CH$_2$), 31.6 (CH$_2$), 31.2 (CH$_2$), 28.9 (CH$_2$), 26.0 (CH$_3$) 25.6 (CH$_2$), 18.4 (quat.), −5.2 (CH$_3$); MS (m/e): 354 (M$^+$2%), 297 (50), 179 (14), 153 (100), 75 (56).

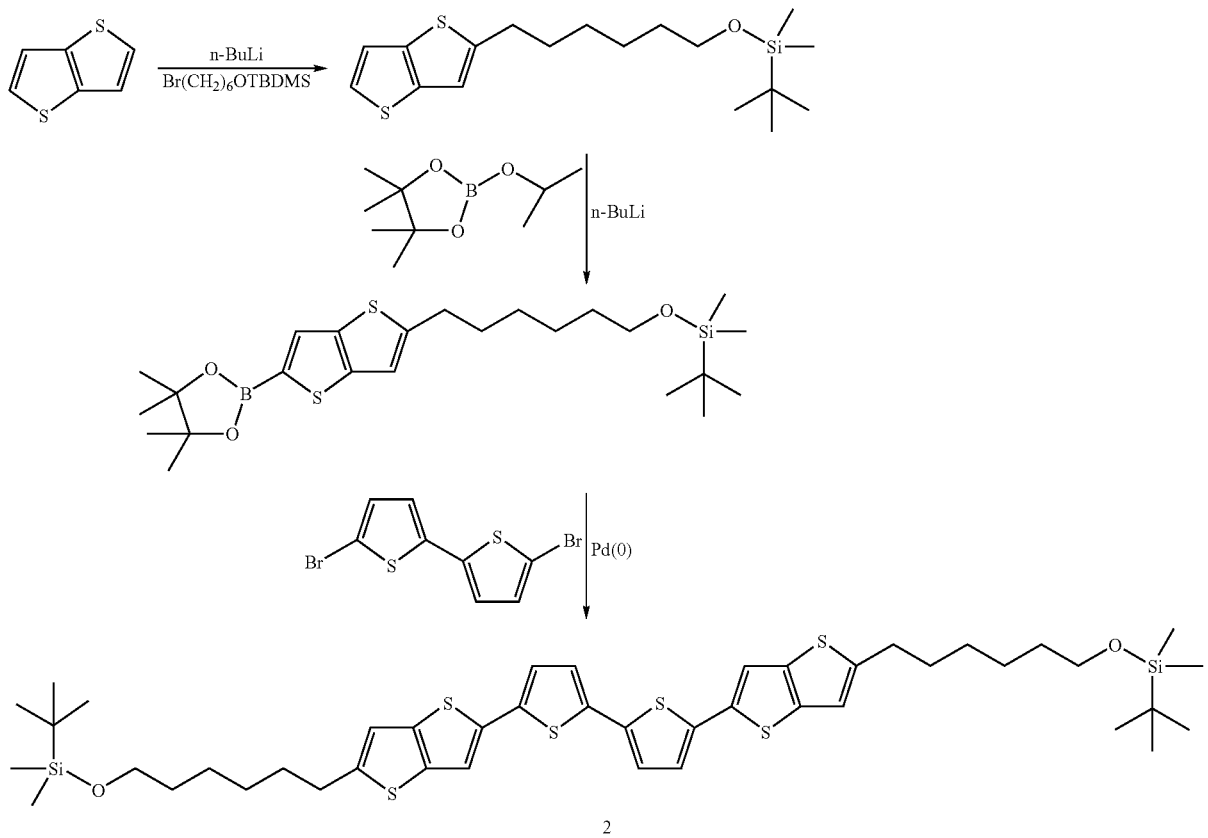

2 tert-Butyldimethyl(6-thieno[3,2-b]thiophen-2-yl-hexyloxy-silane

To a stirred solution of thieno(3,2-b)thiophene (3.15 g, 22.50 mmol) in dry THF (70 ml) was added n-butyllithium (2.5 M in hexanes, 7.50 ml, 18.75 mmol) dropwise at −78° C. under nitrogen. After complete addition, the mixture was allowed to warm to room temperature, with stirring, over 2 h, followed by the addition of 6-bromohexyloxy-tert-butyldimethylsilane (5.53 g, 18.75 mmol). The resultant mixture was stirred overnight at room temperature. The reaction was quenched with sat. aq. ammonium chloride, and the reaction mixture was extracted with ethyl acetate (3×70 ml). The combined organic extracts were washed with water, brine, and dried over magnesium sulphate. The solvent was removed under reduced pressure and the residue was purified by chromatography (silica gel, petroleum/ethyl acetate from 100:0 to 20:1), to give the product as an brown oil (5.61 g, 84%). $^1$H NMR (300 MHz, CDCl$_3$): δ (ppm) 7.23 (d, J=5.2

2-{5-[6-(tert-Butyldimethylsilanyloxy)-hexyl]-thieno [3,2-b]thiophen-2-yl}-4,4,5,5-tetramethyl-[1,3,2] dioxaborolane To an ice-cooled solution of tert-Butyldimethyl(6-thieno [3,2-b]thiophen-2-yl-hexyloxy-silane (5.0 g, 14.10 mmol) in anhydrous THF (70 ml) was added dropwise a solution of n-butyllithium (2.5 M in hexanes, 5.64 ml, 14.10 mmol) under nitrogen, with stirring. After 2 h, pinacol boronate (2.62 g, 14.10 mmol) was added. The ice bath was removed, and the resultant mixture was stirred overnight at room temperature. The reaction was quenched with the addition of saturated aqueous NH$_4$Cl and the mixture extracted with ethyl acetate (3×70 ml). The combined organic extracts were washed with brine, dried over magnesium sulphate, and evaporated under reduced pressure. The residue was purified by column chromatography on silica, eluting with petroleum ether/ethyl acetate (9:1), to give a brown oil (5.53 g, 82%). $^1$H NMR (300 MHz, CDCl$_3$): δ (ppm) 7.68 (s, 1H, Ar—H), 6.99 (s, 1H, Ar—H), 3.60 (t, J=6.4 Hz, 2H, OCH$_2$), 2.86 (t, J=7.9 Hz, 2H, ArCH$_2$), 1.25-1.750 (m, 8H, CH$_2$), 0.90 (s, 9H, CH$_3$), 0.05 (s, 6H, CH$_3$); MS (m/e): 480 (M$^+$, 6%), 423 (17), 253 (54), 179 (37), 153 (37), 83 (100).

5,5'-Bis-{5'-(6-tert-butyldimethylsilanyloxy)-hexyl]-thieno[3,2-b]thiophen-2-yl}-[2,2']-bithiophene (2)

Tetrakis(triphenylphosphine)palladium(0) (0.05 g) was added to a solution 5,5'-dibromo-2,2'-bithiophene (0.10 g, 0.31 mmol) in dry THF (30 ml), with stirring, under nitrogen. After 20 min, 2-{5-[6-(tert-Butyldimethylsilanyloxy)-hexyl]-thieno[3,2-b]thiophen-2-yl}-4,4,5,5-tetramethyl-[1,3,2]dioxaborolane (0.44 g, 0.93 mmol) and a solution of potassium carbonate (0.26 g, 1.88 mmol) in water (10 ml) was added. The resultant mixture was heated at reflux for 1.5 h. After cooling, water (100 ml) was added and the precipitate filtered off, washed with water and diethyl ether, to give a yellow solid, which was recrystallised with toluene to offer yellow crystals (0.19 g, 70%).

LC phases: K-77° C.-S$_X$-192° C.-S$_{X1}$-227° C.-I.

$^1$H NMR (300 MHz, CDCl$_3$): δ (ppm) 7.27 (s, 2H, Ar—H), 7.07 (m, 4H, Ar—H), 6.91 (s, 2H, Ar—H), 3.61 (t, J=6.4 Hz, 4H, OCH$_2$), 2.88 (t, J=7.6 Hz, 4H, ArCH$_2$), 1.37-1.79 (m, 16H, CH$_2$), 0.90 (s, 18H, CH$_3$), 0.05 (s, 12H, CH$_3$); $^{13}$C NMR (75 MHz, CDCl$_3$): δ (ppm) 148.8 (quat.), 137.8 (quat.), 137.7 (quat.), 136.9 (quat.), 136.8 (quat.), 135.8 (quat.), 124.3 (CH), 124.1 (CH), 116.4 (CH), 116.0 (CH), 63.2 (OCH$_2$), 32.8 (CH$_2$), 31.5 (CH$_2$), 31.2 (CH$_2$), 28.9 (CH$_2$), 26.0 (CH$_3$) 25.6 (CH$_2$), 18.4 (quat.), −5.2 (CH$_3$).

EXAMPLE 3

Compound 3 is prepared as outlined below:

1,4-Bis-{5'-(6-tert-butyldimethylsilanyloxy)-hexyl]-thieno[3,2-b]thiophen-2-yl}-benzene (3)

Tetrakis(triphenylphosphine)palladium(0) (0.05 g) was added to a solution 1,4-dibromobenzene (0.10 g, 0.42 mmol) in dry THF (30 ml), with stirring, under nitrogen. After 20 min, 2-{5-[6-(tert-Butyldimethylsilanyloxy)-hexyl]-thieno[3,2-b]thiophen-2-yl}-4,4,5,5-tetramethyl-[1,3,2]dioxaborolane (0.61 g, 1.27 mmol) and a solution of potassium carbonate (0.35 g, 2.54 mmol) in water (10 ml) was added. The resultant mixture was heated at reflux for 1.5 h. After cooling, the reaction mixture was extracted with ethyl acetate (3×50 ml) and the combined extracts dried over magnesium sulphate. The solvent was removed under reduced pressure and the residue washed with diethyl ether in Bush funnel to give a blue solid, which was recrystallised with toluene to afford 3 as light blue crystals (0.16 g, 48%).

LC phases: K 80° C.-K$_1$-134° C.-S$_X$-187° C.-S$_{X1}$-218° C.-I.

$^1$H NMR (300 MHz, CDCl$_3$): δ (ppm) 7.61 (s, 4H, Ar—H), 7.44 (s, 2H, Ar—H), 6.94 (s, 2H, Ar—H), 3.61 (t, J=6.4 Hz, 4H, OCH$_2$), 2.89 (t, J=7.4 Hz, 4H, ArCH$_2$), 1.35-1.83 (m, 16H, CH$_2$), 0.90 (s, 18H, CH$_3$), 0.05 (s, 12H, CH$_3$); $^{13}$C NMR (75 MHz, CDCl$_3$): δ (ppm) 148.4 (quat.), 143.8 (quat.), 138.2 (quat.), 138.1 (quat.), 134.0 (quat.), 126.0 (CH), 116.5 (CH), 115.4 (CH), 63.2 (OCH$_2$), 32.8 (CH$_2$), 31.6 (CH$_2$), 31.2 (CH$_2$), 28.9 (CH$_2$), 26.0 (CH$_3$) 25.6 (CH$_2$), 18.4 (quat.), −5.2 (CH$_3$).

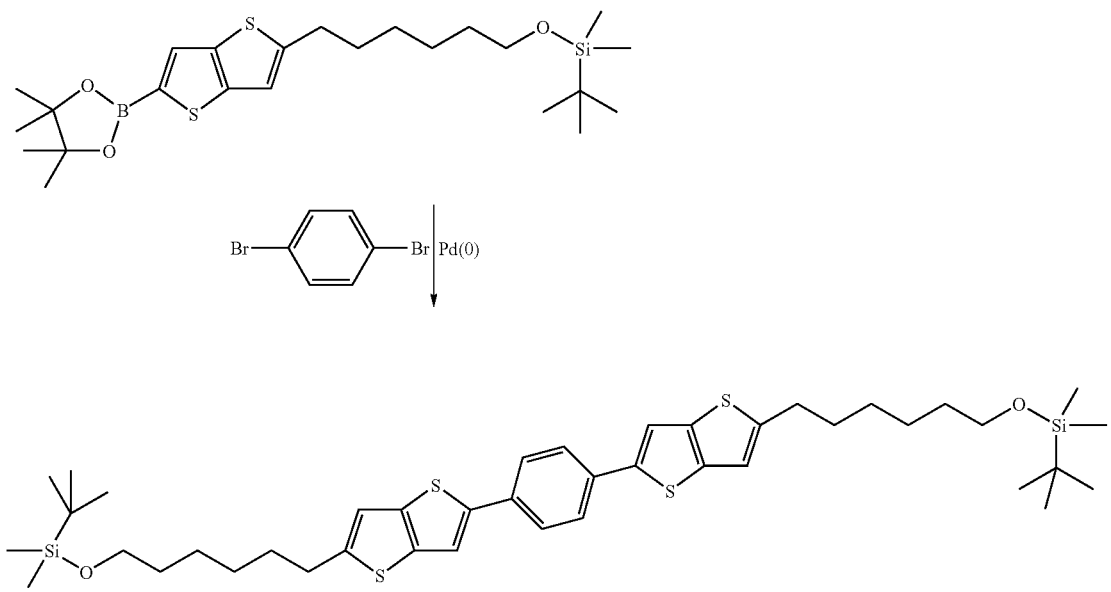

EXAMPLE 4

Compound 4 is prepared as outlined below:

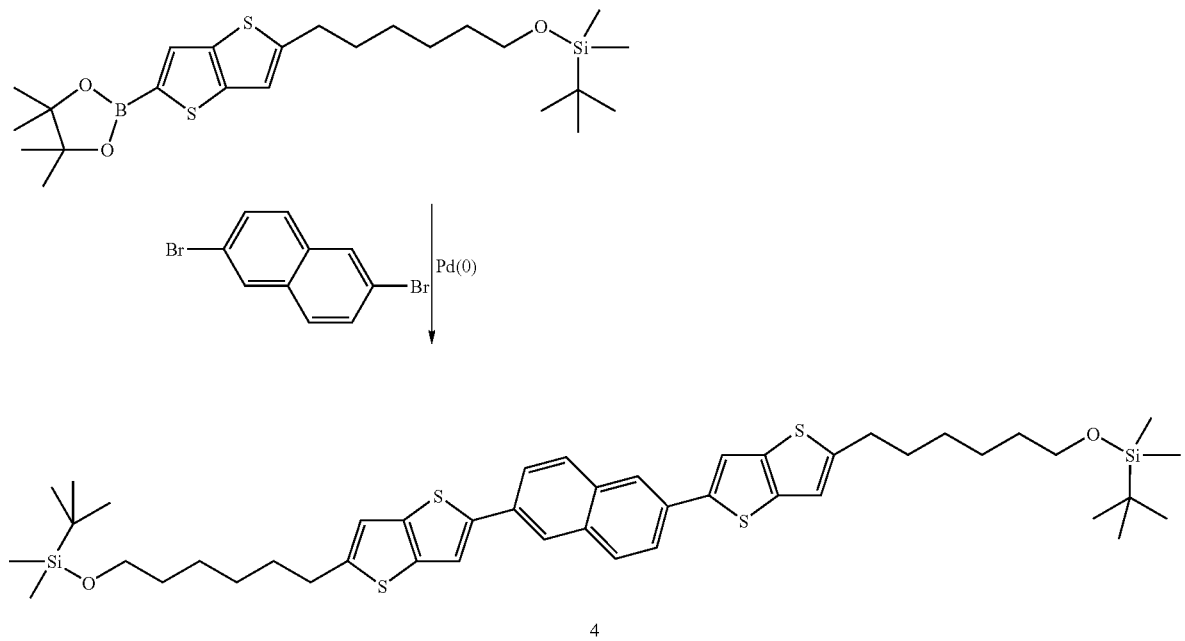

4

2,6-Bis-{5'-(6-tert-butyldimethylsilanyloxy)-hexyl]-thieno[3,2-b]thiophen-2-yl}-naphthalene (4)

Tetrakis(triphenylphosphine)palladium(0) (0.05 g) was added to a solution 2,6-dibromonaphthalene (0.10 g, 0.35 mmol) in dry THF (30 ml), with stirring, under nitrogen. After 20 min, 2-{5-[6-(tert-Butyldimethylsilanyloxy)-hexyl]-thieno[3,2-b]thiophen-2-yl}-4,4,5,5-tetramethyl-[1,3,2]di-oxaborolane (0.50 g, 1.05 mmol) and a solution of potassium carbonate (0.29 g, 2.10 mmol) in water (10 ml) was added. The resultant mixture was heated at reflux for 1.5 h. After cooling, water (100 ml) was added and the precipitate filtered off, washed with water and diethyl ether, to give a blue solid, which was recrystallised with toluene to afford 4 as light blue crystals (0.23 g, 79%).

LC Phases: K-89° C.-$S_X$-228° C.-$S_{X1}$-266° C.-I.

$^1$H NMR (300 MHz, CDCl$_3$): δ (ppm) 7.98 (s, 2H, Ar—H), 7.83 (d, J=8.4 Hz, 2H, Ar—H), 7.75 (d, J=8.4 Hz, 2H, Ar—H), 7.53 (s, 2H, Ar—H), 6.96 (s, 2H, Ar—H), 3.61 (t, J=6.4 Hz, 4H, OCH$_2$), 2.89 (t, J=7.6 Hz, 4H, ArCH$_2$), 1.34-1.80 (m, 16H, CH$_2$), 0.90 (s, 18H, CH$_3$), 0.05 (s, 12H, CH$_3$); $^{13}$C NMR (75 MHz, CDCl$_3$): δ (ppm) 148.5 (quat.), 144.2 (quat.), 138.2 (quat.), 132.9 (quat.), 132.5 (quat.), 128.6 (CH), 124.8 (CH), 123.6 (CH), 116.6 (CH), 115.9 (CH), 63.2 (OCH$_2$), 32.8 (CH$_2$), 31.6 (CH$_2$), 31.2 (CH$_2$), 28.9 (CH$_2$), 26.0 (CH$_3$) 25.6 (CH$_2$), 18.4 (quat.), −5.2 (CH$_3$).

EXAMPLE 5

Compound 5 is prepared as outlined below:

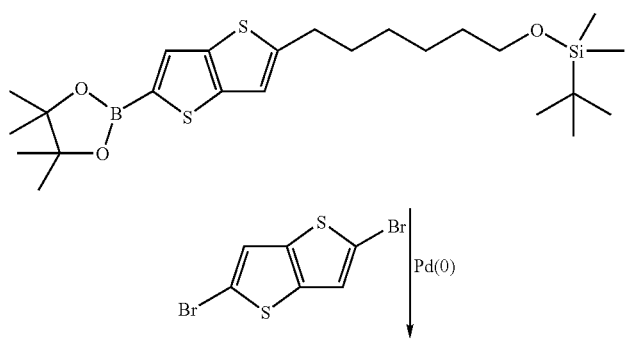

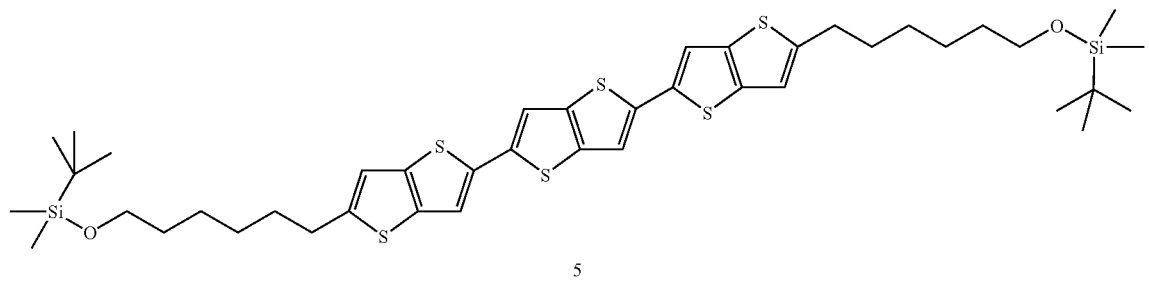

5,5"-Bis-[6-(tert-butyldimethylsilanyloxy)hexyl]-[2,2';3',2"]ter[thieno[3,2-b]thiophene (5)

Tetrakis(triphenylphosphine)palladium(0) (0.05 g) was added to a solution 2,5-dibromothieno[3,2-b]thiophene (0.10 g, 0.34 mmol) in dry THF (30 ml), with stirring, under nitrogen. After 20 min, 2-{5-[6-(tert-Butyldimethylsilanyloxy)-hexyl]-thieno[3,2-b]thiophen-2-yl}-4,4,5,5-tetramethyl-[1,3,2]dioxaborolane (0.49 g, 1.02 mmol) and a solution of potassium carbonate (0.28 g, 2.04 mmol) in water (10 ml) was added. The resultant mixture was heated at reflux for 1.5 h. After cooling, water (100 ml) was added and the precipitate filtered off, washed with water and diethyl ether, to give a yellow solid, which was recrystallised with toluene to give 5 as yellow crystals (0.23 g, 82%).

LC Phases: K-88° C.-$S_X$-229° C.-$S_{X1}$-290° C.-I.

$^1$H NMR (300 MHz, CDCl$_3$): δ (ppm) 7.30 (s, 2H, Ar—H), 7.28 (s, 2H, Ar—H), 6.91 (s, 2H, Ar—H), 3.61 (t, J=6.4 Hz, 4H, OCH$_2$), 2.88 (t, J=7.5 Hz, 4H, ArCH$_2$), 1.35-1.80 (m, 16H, CH$_2$), 0.90 (s, 18H, CH$_3$), 0.05 (s, 12H, CH$_3$); $^{13}$C NMR (75 MHz, CDCl$_3$): δ (ppm) 148.9 (quat.), 139.4 (quat.), 138.4 (quat.), 137.8 (quat.), 137.7 (quat.), 137.3 (quat.), 116.4 (CH), 116.1 (CH), 115.4 (CH), 63.2 (OCH$_2$), 32.8 (CH$_2$), 31.6 (CH$_2$), 31.2 (CH$_2$), 28.9 (CH$_2$), 26.0 (CH$_3$) 25.6 (CH$_2$), 18.4 (quat.), −5.2 (CH$_3$).

The compounds 1-5 of examples 1-5 can be further reacted to give polymerisable monomers by converting the terminal silyl group into e.g. an acrylate or methacrylate group by known methods.

EXAMPLE 6

Compound 6 is prepared as described below:

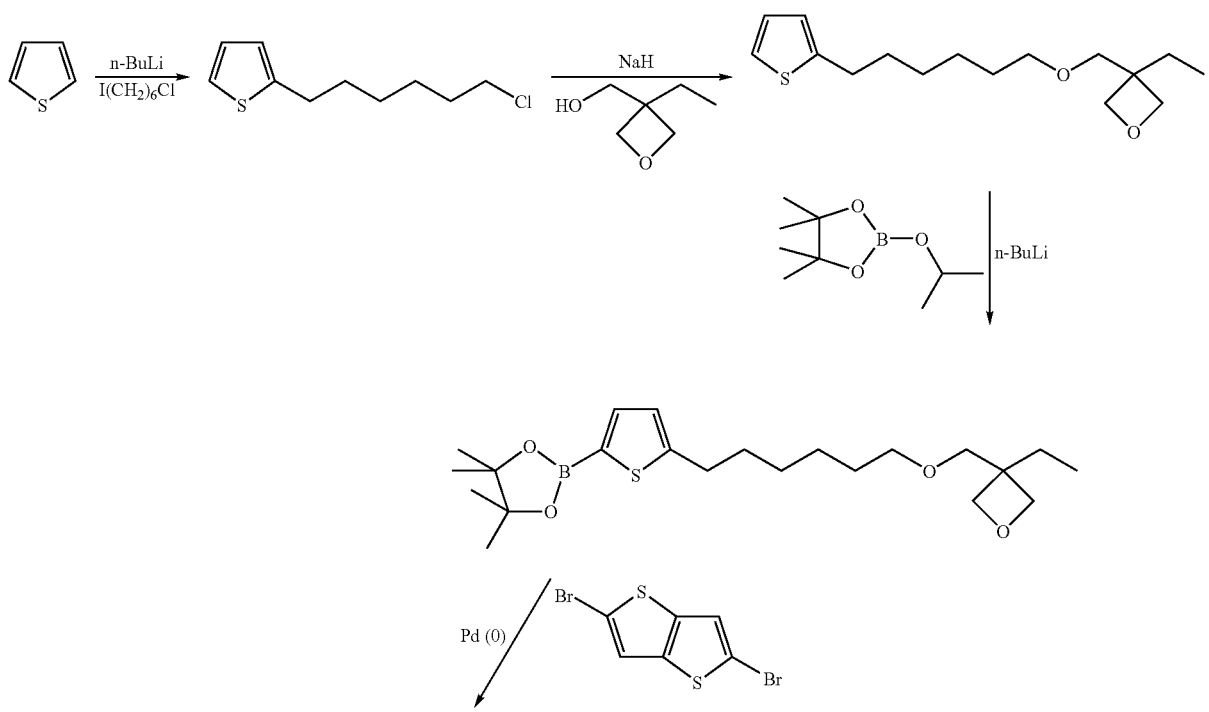

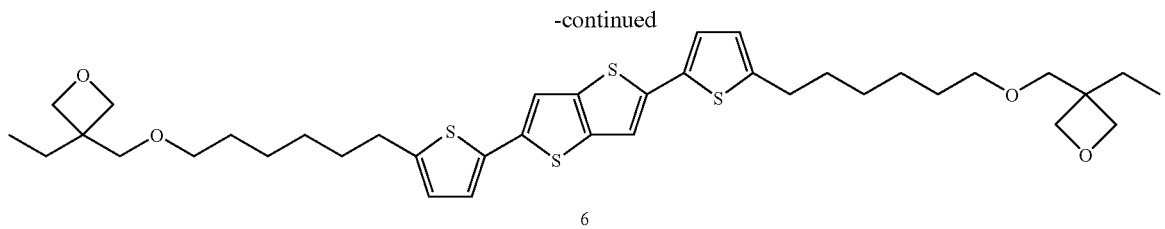

6

2-(6-Chlorohexyl)thiophene

To a stirred solution of thiophene (5.0 g, 59.5 mmol) in dry THF (50 ml) was added n-butyllithium (2.5 M in hexanes, 20.0 ml, 50.0 mmol) dropwise at −78° C. under nitrogen. After complete addition, the mixture was allowed to warm to room temperature, with stirring, over 2 h, followed by the addition of 1-chloro-6-iodohexane (12.3 g, 50.0 mmol). The resultant mixture was stirred overnight at room temperature. The reaction was quenched with sat. aq. ammonium chloride, and the reaction mixture was extracted with ethyl acetate (3×70 ml). The combined organic extracts were washed with water, brine, and dried over magnesium sulphate. The solvent was removed under reduced pressure and the residue was chromatographyed (silica gel, petroleum ether), to afford the product as a pale yellow oil (9.3 g, 92%). $^1$H NMR (300 MHz, CDCl$_3$): δ (ppm) 7.06 (dd, J=5.1 Hz, 1.2 Hz, 1H, Ar—H), 6.87 (dd, J=5.1 Hz, 3.4 Hz, 1H, Ar—H), 6.75 (m, 1H, Ar—H), 3.48 (t, J=6.6 Hz, 2H, ClCH$_2$), 2.80 (t, J=7.4 Hz 2H, ArCH$_2$), 1.61-1.78 (m, 4H, CH$_2$), 1.29-1.50 (m, 4H, CH$_2$); $^{13}$C NMR (75 MHz, CDCl$_3$): δ (ppm) 145.5 (quat.), 126.7 (CH), 124.1 (CH), 122.9 (CH), 45.1 (CH$_2$), 32.6 (CH$_2$), 31.7 (CH$_2$), 29.9 (CH$_2$), 28.4 (CH$_2$) 26.7 (CH$_2$); MS (m/e) 204 (M$^+$, 9%), 202 (M$^+$, 3%), 97 (100).

3-Ethyl-3-(6-thiophen-2-yl-hexyloxymethyl)oxetane

3-Ethyl-3-oxtanemethanol (10.0 g, 86.08 mmol) was added slowly to a suspension of sodium hydride (60% dispersion in mineral oil, 3.44 g, 86.0 mmol) in DMF (150 ml) at 0° C., with stirring, under nitrogen. After complete addition, the ice-bath was removed and the mixture was stirred another 20 min, followed by the addition of 2-(6-chlorohexyl)thiophene (16.22 g, 80.0 mmol). The resultant mixture was stirred overnight, then water (200 ml) was added and the mixture extracted with ethyl acetate (3×100 ml). The combined extracts were washed with water and brine, then dried (Na$_2$SO$_4$) and evaporated under reduced pressure. The residue was purified by column chromatography, eluting with petroleum ether/ethyl acetate (10:0 to 9:1), to afford the product as a brown oil (13.74 g, 61%). $^1$H NMR (300 MHz, CDCl$_3$): δ (ppm) 7.07 (dd, J=5.1 Hz, 1.1 Hz, 1H, Ar—H), 6.88 (dd, J=5.0 Hz, 3.4 Hz, 1H, Ar—H), 6.76 (m, 1H, Ar—H), 4.43 (d, J=5.8 Hz, 2H, OCH$_2$), 4.36 (d, J=5.8 Hz, 2H, OCH$_2$), 3.50 (s, 2H, OCH$_2$), 3.43 (t, J=6.4 Hz, 2H, OCH$_2$), 2.81 (t, J=7.6 Hz 2H, ArCH$_2$), 1.37-1.77 (m, 10H, CH$_2$), 0.87 (t, J=7.6 Hz, 6H, CH$_3$); $^{13}$C NMR (75 MHz, CDCl$_3$): δ (ppm) 145.6 (quat.), 126.6 (CH), 123.9 (CH), 122.7 (CH), 78.5 (OCH$_2$), 73.4 (OCH$_2$), 71.5 (OCH$_2$), 43.4 (quat.), 31.8 (CH$_2$), 29.8 (CH$_2$), 29.5 (CH$_2$), 28.9 (CH$_2$), 26.8 (CH$_2$) 25.9 (CH$_2$), 8.2 (CH$_3$); MS (m/e): 282 (M$^+$, 2%), 166 (8), 123 (39), 110 (22), 97 (100).

2-{5-[6-(3-Ethyl-oxetan-3-ylmethoxy)-hexyl]-thiophen-2-yl}-4,4,5,5-tetramethyl-[1,3,2]dioxaborolane To a stirred solution of 3-ethyl-3-(6-thiophen-2-yl-hexyloxymethyl)oxetane (6.0 g, 21.28 mmol) in dry THF (70 ml) was added n-butyllithium (2.5 M in hexanes, 8.10 ml, 21.28 mmol) dropwise at −78° C. under nitrogen. After complete addition, the mixture was allowed to warm to room temperature, with stirring, over 2 h, followed by the addition of pinacol boronate (3.96 g, 21.28 mmol). The resultant mixture was stirred overnight at room temperature. The reaction was quenched with water, and the reaction mixture was extracted with ethyl acetate (3×70 ml). The combined organic extracts were washed with water, brine, and dried over sodium sulphate. The solvent was removed under reduced pressure and the residue was purified by column chromatography on silica, eluting with petroleum ether/ethyl acetate (9:1), to afford the product as a yellow oil (6.28 g, 72%). $^1$H NMR (300 MHz, CDCl$_3$): δ (ppm) 7.45 (d, J=3.4 Hz, 1H, Ar—H), 6.85 (d, J=3.4 Hz, 1H, Ar—H), 4.44 (d, J=5.8 Hz, 2H, OCH$_2$), 4.36 (d, J=5.8 Hz, 2H, OCH$_2$), 3.51 (s, 2H, OCH$_2$), 3.45 (t, J=6.4 Hz, 2H, OCH$_2$), 2.83 (t, J=7.6 Hz 2H, ArCH$_2$), 1.32-1.77 (m, 22H, CH$_2$ and CH$_3$), 0.88 (t, J=7.4 Hz, 3H, CH$_3$); δ (ppm) 153.5 (quat.), 145.6 (quat.), 137.3 (CH), 125.9 (CH), 83.9 (quat.), 78.6 (OCH$_2$), 73.4 (OCH$_2$), 71.5 (OCH$_2$), 43.4 (quat.), 31.6 (CH$_2$), 30.1 (CH$_2$), 29.4 (CH$_2$), 28.8 (CH$_2$), 26.8 (CH$_2$), 25.9 (CH$_2$), 24.8 (CH$_3$), 8.2 (CH$_3$); MS (m/e): 408 (M$^+$, 0.5%), 223 (27), 165 (30), 141 (35), 123 (100), 97 (52).

2,5-bis{5-[6-(3-Ethyl-oxetan-3-ylmethoxy)-hexyl]-thiophen-2-yl}-thieno[3,2-b]thiophene (6)

Tetrakis(triphenylphosphine)palladium(0) (0.05 g) was added to a solution of 2,5-dibromothieno[3,2-b]thiophene (0.10 g, 0.34 mmol) in dry THF (30 ml), with stirring, under nitrogen. After 20 min, 2-{5'-[6-(3-ethyloxyoxetan-3-ylmethoxy)hexyl]thioen-2-yl}-4,4,5,5-tetramethyl-[1,3,2]dioxaborolane (0.33 g, 0.81 mmol) and a solution of potassium carbonate (0.23 g, 1.67 mmol) in water (5 ml) was added. The resultant mixture was heated at reflux for 1.5 h. After cooling, water (50 ml) was added and the reaction mixture extracted with ethyl acetate (3×50 ml) and the combined extracts dried over sodium sulphate. The solvent was removed under reduced pressure and the residue washed with diethyl ether in Bush funnel to give a yellow solid, which was recrystallised with toluene to afford 6 as yellow crystals (0.13 g, 55%).

LC Phases: K-98° C.-S$_X$-108° C.-I.

$^1$H NMR (300 MHz, CDCl$_3$): δ (ppm) 7.19 (s, 2H, Ar—H), 7.01 (d, J=3.6 Hz, 2H, Ar—H), 6.69 (d, J=3.6 Hz, 2H, Ar—H), 4.45 (d, J=5.9 Hz, 4H, OCH$_2$), 4.38 (d, J=5.9 Hz, 4H, OCH$_2$), 3.52 (s, 4H, OCH$_2$), 3.45 (t, J=6.4 Hz, 4H, OCH$_2$), 2.80 (t, J=7.3 Hz 4H, ArCH$_2$), 1.35-1.78 (m, 20H, CH$_2$), 0.88 (t, J=7.5 Hz, 6H, CH$_3$); $^{13}$C NMR (75 MHz, CDCl$_3$): δ (ppm) 145.6 (quat.), 139.1 (quat.), 138.0 (quat.), 135.1 (quat.), 124.9

(CH), 123.5 (CH), 115.0 (CH), 78.7 (OCH$_2$), 73.4 (OCH$_2$), 71.5 (OCH$_2$), 43.4 (quat.), 31.6 (CH$_2$), 30.2 (CH$_2$), 29.5 (CH$_2$), 28.9 (CH$_2$), 26.8 (CH$_2$) 25.9 (CH$_2$), 8.3 (CH$_3$).

EXAMPLE 7

Compound (7) is prepared as described below:

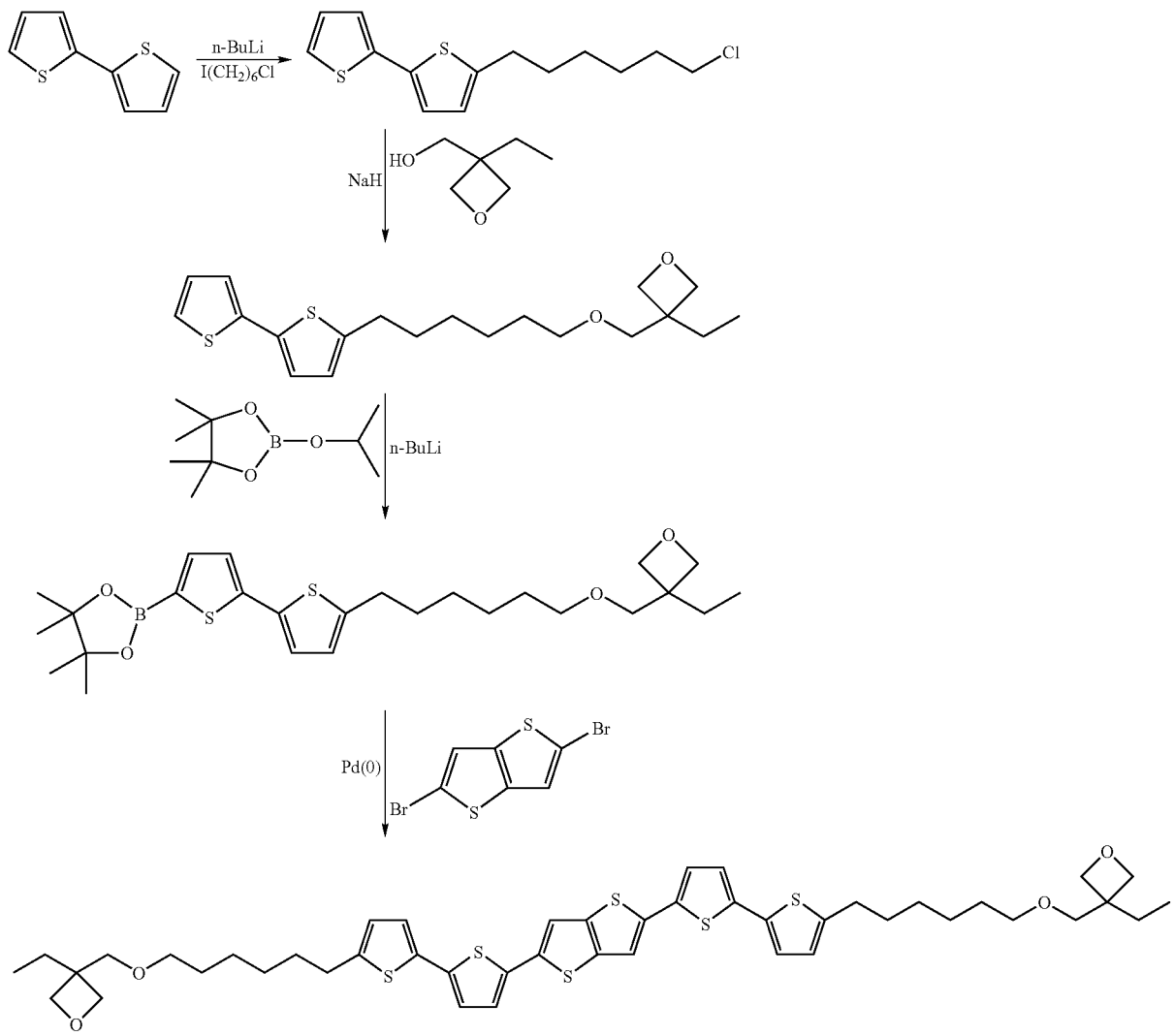

7

5-(6-Chlorohexyl)-2,2'-bithiophene

To a stirred solution of 2,2'-bithiophene (10.0 g, 60.24 mmol) in anhydrous THF (150 ml) was added n-butyllithium (2.5 M in hexanes, 20.0 ml, 50.0 mmol) dropwise at −78° C. under nitrogen. After complete addition, the mixture was allowed to warm to room temperature, with stirring, over 2 h, followed by the addition of 1-chloro-6-iodohexane (14.55 g, 50.0 mmol). The resultant mixture was stirred overnight at room temperature. The reaction was quenched with sat. aq. NH$_4$Cl, and the reaction mixture was extracted with ethyl acetate (3×100 ml). The combined organic extracts were washed with water, brine, and dried over sodium sulphate. The solvent was removed under reduced pressure and the residue was purified by column chromatography on silica, eluting with petroleum ether, to give 5-(6-chlorohexyl)-2,2'-bithiophene as a white solid (7.73 g, 54%). $^1$H NMR (300 MHz, CDCl$_3$): δ (ppm) 7.14 (d, J=5.3 Hz, 1.3 Hz, 1H, Ar—H), 7.08 (dd, J=3.5 Hz, 1.1 Hz, 1H, Ar—H), 6.97 (m, 2H, Ar—H), 6.66 (d, J=3.5 Hz, 1H, Ar—H), 3.51 (d, J=6.6 Hz, 2H, ClCH$_2$), 2.78 (t, J=7.1 Hz 2H, ArCH$_2$), 1.61-1.81 (m, 4H, CH$_2$), 1.35-1.51 (m, 4H, CH$_2$); MS (m/e): 282 (M$^+$, 2%), 166 (8), 123 (39), 110 (22), 97 (100).

3-(6-[2,2']Bithiophenyl-5-yl-hexyloxymethyl)-3-ethyl-oxetane

3-Ethyl-3-oxtanemethanol (3.10 g, 26.72 mmol) was added slowly to a suspension of sodium hydride (60% dispersion in mineral oil, 1.07 g, 26.72 mmol) in DMF (70 ml) at 0° C., with stirring, under nitrogen. After complete addition, the ice-bath was removed and the mixture was stirred another 20 min, followed by the addition of 5-(6-chlorohexyl)-2,2'-bithiophene (7.61 g, 26.72 mmol). The resultant mixture was stirred overnight, then water (100 ml) was added and the mixture extracted with ethyl acetate (3×70 ml). The combined extracts were washed with water and brine, then dried ($Na_2SO_4$) and evaporated under reduced pressure. The residue was purified by column chromatography, eluting with petroleum ether/ethyl acetate (100:0 to 9:1), to give 3-(6-[2,2']bithiophenyl-5-yl-hexyloxymethyl)-3-ethyl-oxetane as a brown oil (6.34 g, 65%). $^1$H NMR (300 MHz, $CDCl_3$): δ (ppm) 7.15 (dd, J=5.0 Hz, 1.1 Hz, 1H, Ar—H), 7.05 (dd, J=3.6 Hz, 1.1 Hz, 1H, Ar—H), 6.92 (m, 2H, Ar—H), 6.62 (d, J=3.4 Hz, 1H, Ar—H), 4.40 (d, J=5.9 Hz, 2H, $OCH_2$), 4.32 (d, J=5.9 Hz, 2H, $OCH_2$), 3.45 (s, 2H, $OCH_2$), 3.38 (t, J=6.4 Hz, 2H, $OCH_2$), 2.73 (t, J=7.6 Hz 2H, $ArCH_2$), 1.32-1.73 (m, 10H, $CH_2$), 0.84 (t, J=7.5 Hz, 6H, $CH_3$); $^{13}$C NMR (75 MHz, $CDCl_3$): δ (ppm) 144.9 (quat.), 137.9 (quat.), 134.8 (quat.), 127.7 (CH), 124.8 (CH), 123.6 (CH), 123.3 (CH), 122.9 (CH), 78.4 ($OCH_2$), 73.4 ($OCH_2$), 71.4 ($OCH_2$), 43.4 (quat.), 31.6 ($CH_2$), 30.1 ($CH_2$), 29.5 ($CH_2$), 28.9 ($CH_2$), 26.8 ($CH_2$) 26.0 ($CH_2$), 8.2 ($CH_3$). 364 ($M^+$, 13%), 205 (11), 179 (100).

2-{5'-[6-(3-Ethyl-oxetan-3-ylmethoxy)hexyl]-[2,2']bithiophenyl-5-yl}-4,4,5,5-tetramethyl-[1,3,2]dioxaborolane To a stirred solution of 3-(6-[2,2']bithiophenyl-5-yl-hexyloxymethyl)-3-ethyl-oxetane (6.0 g, 16.46 mmol) in anhydrous THF (100 ml) was added n-butyllithium (2.5 M in hexanes, 7.0 ml, 17.50 mmol) dropwise at −78° C. under nitrogen. After complete addition, the mixture was allowed to warm to room temperature, with stirring, over 2 h, followed by the addition of 2-isopropoxy-4,4,5,5-tetramethyl-1,3,2-dioxaborolane (3.26 g, 17.5 mmol). The resultant mixture was stirred overnight at room temperature. The reaction was quenched with sat. aq. $NH_4Cl$, and the reaction mixture was extracted with ethyl acetate (3×100 ml). The combined organic extracts were washed with water, brine, and dried over sodium sulphate. The solvent was removed under reduced pressure and the residue was purified by column chromatography on silica, eluting with petroleum ether/ethyl acetate (9:1 to 4:1), to give 2-{5'-[6-(3-ethyl-oxetan-3-ylmethoxy)hexyl]-[2,2']bithiophenyl-5-yl}-4,4,5,5-tetramethyl-[1,3,2]dioxaborolane as a blue oil (4.53 g, 56%). $^1$H NMR (300 MHz, $CDCl_3$): δ (ppm) 7.49 (d, J=3.6 Hz, 1H, Ar—H), 7.14 (d, J=3.6 Hz, 1H, Ar—H), 7.03 (d, J=3.6 Hz, 1H, Ar—H), 6.66 (d, J=3.6 Hz, 1H, Ar—H), 4.43 (d, J=5.8 Hz, 2H, $OCH_2$), 4.34 (d, J=5.8 Hz, 2H, $OCH_2$), 3.48 (s, 2H, $OCH_2$), 3.42 (t, J=6.6 Hz, 2H, $OCH_2$), 2.76 (t, J=7.5 Hz, 2H, $ArCH_2$), 1.32-1.75 (m, 22H, $CH_2$ and $CH_3$), 0.86 (t, J=7.5 Hz, 3H, $CH_3$); $^{13}$C NMR (75 MHz, $CDCl_3$): δ (ppm) 144.8 (quat.), 143.7 (quat.), 137.0 (CH), 133.7 (quat.), 124.0 (CH), 123.1 (CH), 123.0 (CH), 83.1 (quat.), 77.5 ($OCH_2$), 72.4 ($OCH_2$), 70.4 ($OCH_2$), 42.4 (quat.), 31.5 ($CH_2$), 30.5 ($CH_2$), 29.1 ($CH_2$), 28.4 ($CH_2$), 27.8 ($CH_2$) 25.8 ($CH_2$), 24.9 ($CH_3$), 8.3 ($CH_3$); MS (m/e): 490 ($M^+$, 16%) □305 (79), 223 (25), 205 (100).

2,5-Bis-{5'-[6-(3-ethyl-oxetan-3-ylmethoxy)hexyl]-[2,2']bithiophenyl-5-yl}-thieno[3,2-b]thiophene (7)

Tetrakis(triphenylphosphine)palladium (0.01 g) was added to a solution of 2,5-dibromothieno[3,2-b]thiophene (0.11 g, 0.37 mmol) in dry THF (30 ml), with stirring, under nitrogen. After 20 min, 2-{5'-[6-(3-ethyl-oxetan-3-ylmethoxy)hexyl]-[2,2']bithiophenyl-5-yl}-4,4,5,5-tetramethyl-[1,3,2]dioxaborolane (0.59 g, 1.20 mmol) and a solution of potassium carbonate (0.33 g, 2.39 mmol) in water (10 ml) was added. The resultant mixture was heated at reflux for 1.5 h. After cooling, water (50 ml) was added. The precipitate was filtered off and washed with diethyl ether to give brown solid, which was recrystallised with toluene to offer red crystals (0.18 g, 58%).

LC Phases: K-197° C.-$S_X$-237° C.-I.

$^1$H NMR (300 MHz, $CDCl_3$): δ (ppm) 7.22 (s, 2H, Ar—H), 7.08 (d, J=3.5 Hz, 2H, Ar—H), 7.01 (m, 4H, Ar—H), 6.70 (d, J=3.4 Hz, 2H, Ar—H), 4.45 (d, J=5.6 Hz, 4H, $OCH_2$), 4.38 (d, J=5.6 Hz, 4H, $OCH_2$), 3.53 (s, 4H, $OCH_2$), 3.46 (t, J=6.4 Hz, 4H, $OCH_2$), 2.80 (t, J=7.3 Hz, 4H, $ArCH_2$), 1.35-1.78 (m, 20H, $CH_2$), 0.88 (t, J=7.3 Hz, 6H, $CH_3$); $^{13}$C NMR (75 MHz, $CDCl_3$): δ (ppm) $^{13}$C NMR (75 MHz, $CDCl_3$): δ (ppm) 145.7 (quat.), 138.8 (quat.), 138.4 (quat.), 137.2 (quat.), 135.6 (quat.), 134.4 (quat.), 125.0 (CH), 124.4 (CH), 123.6 (CH), 123.57 (CH), 115.5 (CH), 78.7 ($OCH_2$), 73.4 ($OCH_2$), 71.5 ($OCH_2$), 43.4 (quat.), 31.5 ($CH_2$), 30.2 ($CH_2$), 29.5 ($CH_2$), 28.9 ($CH_2$) 26.8 ($CH_2$), 25.9 ($CH_2$), 8.3 ($CH_3$).

EXAMPLE 8

Compound (8) is prepared as described below:

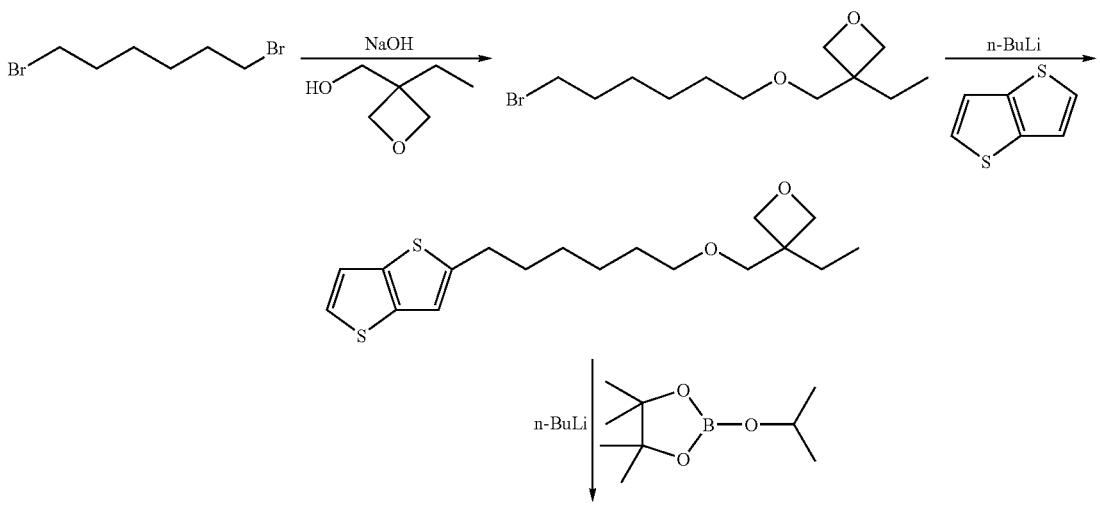

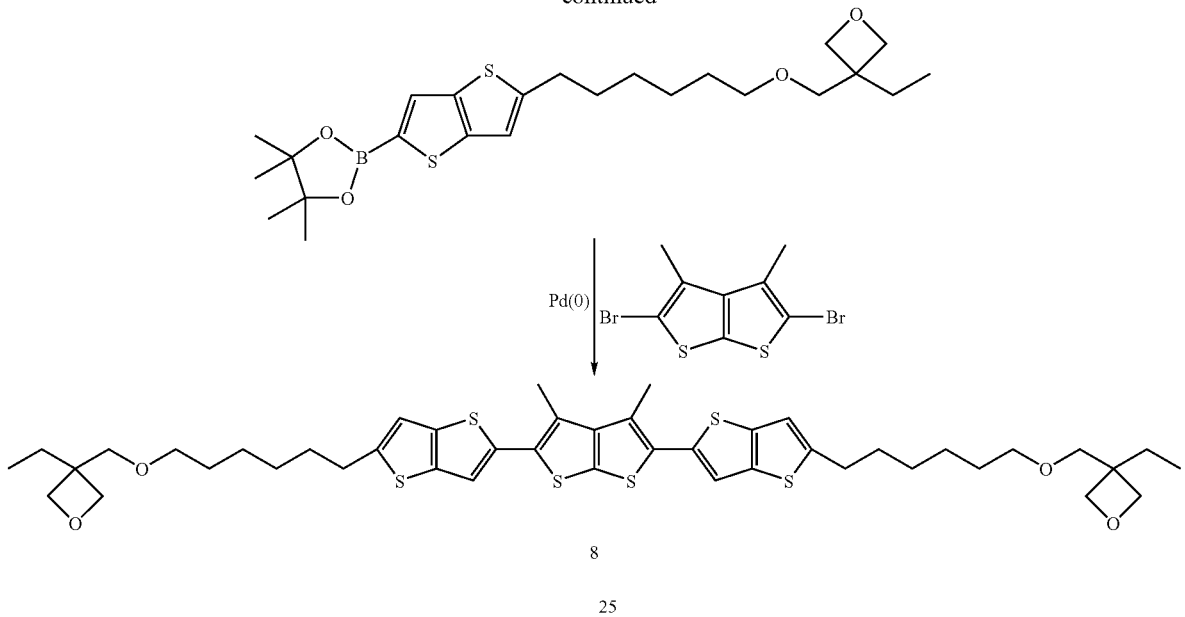

8

3-(6-Bromohexyloxymethyl)-3-ethyloxetane

To a solution consisting of sodium hydroxide (50% in water, 50 g), hexane (50 ml) and tetrabutylammonium bromide (0.7 g) was added 3-ethyl-3-oxetanemethanol (5.0 g, 43.0 mmol) and 1,6-dibromohexane (30 g, 122.9 mmol). This mixture was heated at reflux for 5 h. After cooling to room temperature, the resulting mixture was diluted with water (100 ml) and extracted with ethyl acetate (3×100 ml). The extracts were combined and dried over sodium sulphate. The solvent was removed under reduced pressure and the residue was purified by column chromatography, eluting with petrol/ethyl acetate (9:1), to give a colourless oil (6.65 g, 55%). $^1$H NMR (300 MHz, CDCl$_3$): δ (ppm) 4.44 (d, J=5.8 Hz, 2H, OCH$_2$), 4.37 (d, J=5.8 Hz, 2H, OCH$_2$), 3.52 (s, 2H, OCH$_2$), 3.46 (t, J=6.4 Hz, 2H, OCH$_2$), 3.40 (t, J=6.8 Hz 2H, BrCH$_2$), 1.35-1.91 (m, 10H, CH$_2$), 0.88 (t, J=7.5 Hz, 6H, CH$_3$); $^{13}$C NMR (75 MHz, CDCl$_3$): δ (ppm) 78.5 (OCH$_2$), 73.4 (OCH$_2$), 71.3 (OCH$_2$), 43.4 (quat.), 33.8 (CH$_2$), 32.7 (CH$_2$), 29.3 (CH$_2$), 27.9 (CH$_2$) 26.8 (CH$_2$), 25.4 (CH$_2$), 8.2 (CH$_3$). MS (m/e): 279 (MH$^+$, 0.1%) ☐281 (MH$^+$, 0.1%), 248 (3), 250 (3), 83 (89), 55 (100), 41 (86).

3-Ethyl-3-(6-thieno[3,2-b]thiophen-2-yl-hexyloxymethyl)oxetane

To a stirred solution of thieno(3,2-b)thiophene (5.0 g, 35.7 mmol) in anhydrous THF (120 ml) was added n-butyllithium (2.5 M in hexanes, 12.0 ml, 30.0 mmol) dropwise at −78° C. under nitrogen. After complete addition, the mixture was allowed to warm to room temperature, with stirring, over 2 h, followed by the addition of 3-(6-bromohexyloxymethyl)-3-ethyloxetane (8.38 g, 30.0 mmol). The resultant mixture was stirred overnight at room temperature. The reaction was quenched with sat. aq. NH$_4$Cl, and the reaction mixture was extracted with ethyl acetate (3×70 ml). The combined organic extracts were washed with water, brine, and dried over magnesium sulphate. The solvent was removed under reduced pressure and the residue was purified by column chromatography on silica, eluting with petroleum ether/ethyl acetate (9:1), to give a yellow oil (7.82 g, 77%). $^1$H NMR (300 MHz, CDCl$_3$): δ (ppm) 7.22 (d, J=5.3 Hz, 1H, Ar—H), 7.14 (d, J=5.3 Hz, 1H, Ar—H), 6.91 (s, 1H, Ar—H), 4.43 (d, J=5.8 Hz, 2H, OCH$_2$), 4.35 (d, J=5.8 Hz, 2H, OCH$_2$), 3.48 (s, 2H, OCH$_2$), 3.41 (t, J=6.4 Hz, 2H, OCH$_2$), 2.84 (t, J=7.4 Hz 2H, ArCH$_2$), 1.35-1.75 (m, 10H, CH$_2$), 0.86 (t, J=7.6 Hz, 3H, CH$_3$); $^{13}$C NMR (75 MHz, CDCl$_3$): δ (ppm) 148.3 (quat.), 138.8 (quat.), 137.4 (quat.), 125.4 (CH), 119.5 (CH), 116.3 (CH), 78.6 (OCH$_2$), 73.4 (OCH$_2$), 71.5 (OCH$_2$), 43.4 (quat.), 31.6 (CH$_2$), 31.2 (CH$_2$), 29.5 (CH$_2$), 28.9 (CH$_2$) 26.8 (CH$_2$), 26.0 (CH$_2$), 8.3 (CH$_3$); MS (m/e): 490 (M$^+$, 16%) ☐305 (79), 223 (25), 205 (100).

2-{5-[6(3-Ethyloxetan-3-ylmethoxy)hexyl]-thieno[3,2-b]thiophen-2-yl}4,4,5,5-tetramethyl-1,3,2]dioxaborane To a stirred solution of 3-Ethyl-3-(6-thieno[3,2-b] thiophen-2-yl-hexyloxymethyl)-oxetane (5.0 g, 14.8 mmol) in anhydrous THF (70 ml) was added n-butyllithium (2.5 M in hexanes, 7.2 ml, 18.0 mmol) dropwise at 78° C. under nitrogen. After complete addition, the mixture was allowed to warm to room temperature, with stirring, over 2 h, followed by the addition of 2-isopropoxy-4,4,5,5-tetramethyl-[1,3,2]-dioxaborolane (3.35 g, 18 mmol). The resultant mixture was stirred overnight at room temperature. The reaction was quenched with sat. aq. NH$_4$Cl, and the reaction mixture was extracted with ethyl acetate (3×70 ml). The combined organic extracts were washed with water, brine, and dried over Na$_2$SO$_4$. The solvent was removed under reduced pressure and the residue was purified by column chromatography on silica, eluting with petroleum ether/ethyl acetate (9:1 to 5:1), to give product as a yellow oil (3.72 g, 54%). $^1$H NMR (300 MHz, CDCl$_3$): δ (ppm) 7.67 (s, 1H, Ar—H), 6.94 (s, 1H, Ar—H), 4.42 (d, J=5.8 Hz, 2H, OCH$_2$), 4.36 (d, J=5.8 Hz, 2H, OCH$_2$), 3.48 (s, 2H, OCH$_2$), 3.42 (t, J=6.4 Hz, 2H, OCH$_2$), 2.85 (t, J=7.4 Hz 2H, ArCH$_2$), 1.25-1.75 (m, 22H, CH$_2$), 0.86 (t, J=7.6 Hz, 3H, CH$_3$); $^{13}$C NMR (75 MHz, CDCl$_3$): δ (ppm) 151.2 (quat.), 145.2 (quat.), 138.8 (quat.), 129.1 (CH), 116.4 (CH), 84.0 (quat.), 78.5 (OCH$_2$), 73.3 (OCH$_2$), 71.4 (OCH$_2$), 43.3 (quat.), 31.3 (CH$_2$), 29.5 (CH$_2$), 29.4 (CH$_2$), 28.8 (CH$_2$), 26.7 (CH$_2$), 25.9 (CH$_2$), 24.7 (CH$_3$), 8.2 (CH$_3$); MS (m/e): 464 (M$^+$, 2%) ☐279 (49), 197 (29), 170 (100), 153 (33).

2,5-Bis-{5'-[6-(3-ethyl-oxetan-3-ylmethoxy)hexyl]thieno[3,2-b]thiophen-2-yl}-3,4-dimethylthieno[2,3-b]thiophene (8)

Tetrakis(triphenylphosphine)palladium (0.01 g) was added to a solution of 2,5-dibromo-3,4-dimethylthien(2,3-b)thiophene (0.14 g, 0.43 mmol) in anhydrous toluene (30 ml), with stirring, under nitrogen. After 10 min, 2-{5-[6-(3-ethyloxetan-3-ylmethoxy)hexyl]-thioen[3,2-b]thiophen-2-yl}-4,4,5,5-tetramethy[1,3,2]dioxa-borolane (0.80 g, 1.72 mmol) and a solution of potassium phosphate (0.74 g, 3.49 mmol) in water (10 ml) was added. The resultant mixture was heated at reflux for 2 h. After cooling, water (50 ml) was added and the reaction mixture was extracted with ethyl acetate (3×50 ml) and the combined extracts dried over sodium sulphate. The solvent was removed under reduced pressure and the residue washed with diethyl ether to give a yellow solid, which was recrystallised with ethyl acetate to offer yellow crystals (0.17 g, 47%).

LC Phases: K-114° C.-$S_X$-197° C.-I.

$^1$H NMR (300 MHz, CDCl$_3$): δ (ppm) 7.20 (s, 2H, Ar—H), 6.93 (s, 2H, Ar—H), 4.45 (d, J=5.8 Hz, 4H, OCH$_2$), 4.37 (d, J=5.8 Hz, 4H, OCH$_2$), 3.52 (s, 4H, OCH$_2$), 3.45 (t, J=6.4 Hz, 4H, OCH$_2$), 2.89 (t, J=7.4 Hz, 4H, ArCH$_2$), 2.63 (s, 6H, ArCH$_3$), 1.37-1.78 (m, 20H, CH$_2$), 0.88 (t, J=7.6 Hz, 6H, CH$_3$); $^{13}$C NMR (75 MHz, CDCl$_3$): δ (ppm) 148.5 (quat.), 148.0 (quat.), 139.1 (quat.), 137.4 (quat.), 135.9 (quat.), 135.0 (quat.), 133.2 (quat.), 128.5 (quat.), 119.3 (CH), 116.3 (CH), 78.6 (OCH$_2$), 73.5 (OCH$_2$), 71.5 (OCH$_2$), 43.5 (quat.), 31.5 (CH$_2$), 31.1 (CH$_2$), 29.5 (CH$_2$), 28.8 (CH$_2$) 26.8 (CH$_2$), 25.9 (CH$_2$), 14.3 (CH$_3$), 8.2 (CH$_3$).

The invention claimed is:

1. A compound of formula I

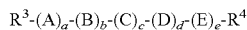

wherein

A, B, C, D and E are independently of each other a TT group of formula II

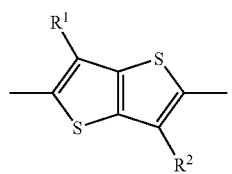

or are selected from phenylene-1,4-diyl that is optionally substituted by one or two R$^1$ groups that are different than H, thiophene-2,5-diyl that is optionally substituted by one or two R$^1$ groups that are different than H, selenophene-2,5-diyl that is optionally substituted by one or two R$^1$ groups that are different than H, and naphthalene-2,6-diyl that is optionally substituted by one or two R$^1$ groups that are different than H, R$^1$ and R$^2$ independently of each other are each H, halogen, P-Sp-, P*-Sp, or straight chain, branched or cyclic alkyl with 1 to 20 C-atoms, which may be unsubstituted, mono- or polysubstituted by F, Cl, Br, I or CN, and wherein one or more non-adjacent CH$_2$ groups are each independently optionally replaced by —O—, —S—, —NH—, —NR$^0$—, —SiR$^0$R$^{00}$—, —CO—, —COO—, —OCO—, —O—CO—O—, —S—CO—, —CO—S—, —CX$^1$=CX$^2$— or —C≡C— in such a manner that O and/or S atoms are not linked directly to one another, R$^3$ and R$^4$ are independently of each other P-Sp-, P*-Sp-, H, halogen, or straight chain, branched or cyclic alkyl with 1 to 20 C-atoms, which may be unsubstituted, mono- or polysubstituted by F, Cl, Br, I or CN, and wherein one or more non-adjacent CH$_2$ groups are each independently optionally replaced by —O—, —S—, —NH—, —NR$^0$—, —SiR$^0$R$^{00}$—, —CO—, —COO—, —OCO—, —O—CO—O—, —S—CO—, —CO—S—, —CX$^1$=CX$^2$— or —C≡C— in such a manner that O and/or S atoms are not linked directly to one another, with at least one of R$^3$ and R$^4$ being P-Sp- or P*Sp—, X$^1$ and X$^2$ are independently of each other H, F, Cl or CN, P is CH$_2$=CH—COO—, CH$_2$=C(CH$_3$)—COO—, CH$_2$=CH—, CH$_2$=CH—O—, (CH$_2$=CH)$_2$CH—OCO—, (CH$_2$=CH)$_2$CH—O—,

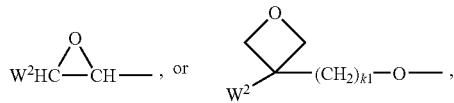

k$_1$ is 0 or 1,

P* is —OH or —O—Si—R$^0$R$^{00}$R$^{000}$,

Sp is a spacer group or a single bond,

R$^0$, R$^{00}$ and R$^{000}$ are independently of each other H, alkyl with 1 to 12 C-atoms or aryl, and a, b, c and d are independently of each other 0, 1, 2 or 3, with a+b+c+d >0;

wherein the compound comprises two or three TT groups, or the compound comprises one, two or three TT groups and one, two, three or four groups selected from phenylene-1,4-diyl, thiophene-2,5-diyl, selenophene-2,5-diyl, and naphthalene-2,6-diyl which in each case is optionally substituted by one or two R$^1$ groups that are different than H.

2. A compound according to claim 1, wherein groups A, B, C, D and E that are not TT are each independently selected from 1,4-phenylene, fluorinated 1,4-phenylene, 2,5-pyridine, 2,5-pyrimidine, p,p'-biphenyl, naphthalene-2,6-diyl, thiophene-2,5-diyl, selenophene-2,5-diyl, fluorinated or alkylated thiophene-2,5-diyl or selenophene-2,5-diyl, 2,2-dithiophene, fluorinated or alkylated 2,2'-dithiophene, fluorinated benzo[1,2-b:4,5-b']dithiophene, 2,5-thiazole, 2,5-thiadiazole, 2,5-oxazole and 2,5-oxadiazole, which in each case are unsubstituted, or mono- or polysubstituted with L, and L is F, Cl, Br, or an alkyl having 1 to 12 C atoms, alkoxy having 1 to 12 C atoms, alkylcarbonyl having up to 12 C atoms, or alkoxycarbonyl having up to 12 C atoms, wherein one or more H atoms are each optionally replaced by F or Cl.

3. A compound according to claim 1, wherein R$^1$ and R$^2$ are each H.

4. A compound according to claim 1, wherein R$^3$ and R$^4$ are each P-Sp- or P*-Sp-.

5. A compound according to claim 1, wherein said compound is selected from the following formulae

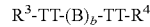  I-1

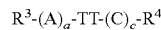  I-2 wherein a, b and c are each 1 or 2.

6. A compound according to claim 1, wherein said compound is selected from the following formulae

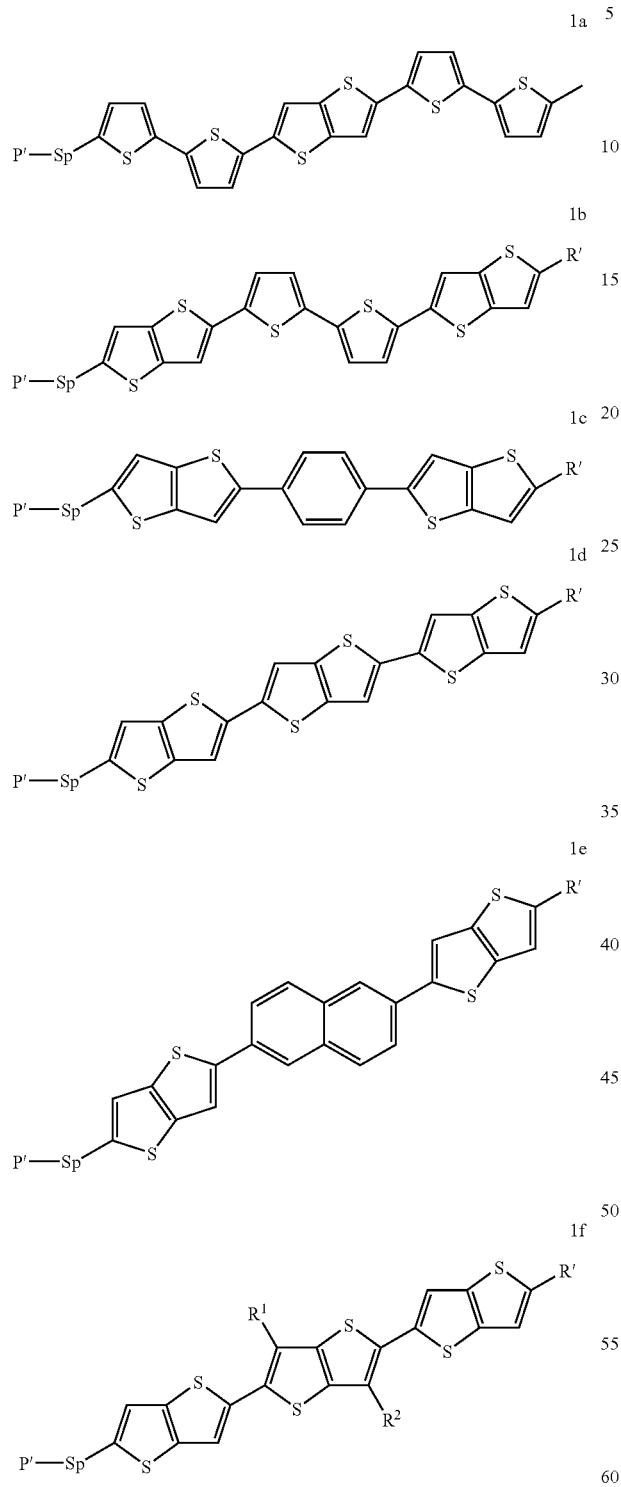

wherein
P' is a polymerizable or reactive group, or a group that can be converted into or substituted by a polymerizable or reactive group, or a protected form of a polymerizable or reactive group, and R' is P-Sp-, P*-Sp-, H, halogen, optionally substituted aryl, optionally substituted heteroaryl, or straight chain, branched or cyclic alkyl with 1 to 20 C-atoms, which may be unsubstituted, mono- or polysubstituted by F, Cl, Br, I or CN, and wherein one or more non-adjacent $CH_2$ groups are each independently optionally replaced by —O—, —S—, —NH—, —NR$^o$—, —SiR$^o$R$^{oo}$—, —CO—, —COO—, —OCO—, —O—CO—O—, —S—CO—, —CO—S—, —CX$^1$=CX$^2$— or —C≡C— in such a manner that O and/or S atoms are not linked directly to one another, with at least one of R$^3$ and R$^4$ being P-Sp- or P*-Sp-.

7. A polymerizable liquid crystal material comprising:
   one or more compounds according to claim 1 and optionally one or more further polymerizable compounds,
   wherein at least one of said one or more compounds of claim 1 and/or said one or more further polymerizable compounds is mesogenic or liquid crystalline.

8. An aniostropic polymer film with charge transport properties obtainable from a polymerizable liquid crystal material according to claim 7 that is aligned in its liquid crystal phase into macroscopically uniform orientation, and polymerized or crosslinked to fix the oriented state.

9. A side chain liquid crystal polymer obtained by polymerization of one or more compounds or a polymerizable material according to claim 1 or by grafting one or more compounds or a polymerizable material according to claim 1 to a polymer backbone in a polymeranaloguous reaction, optionally with one or more additional mesogenic or non-mesogenic comonomers.

10. In a charge-transport, semiconducting, electrically conducting, photoconducting or light-emitting material in optical, electrooptical or electronic components or devices, organic field effect transistors (OFET), integrated circuitry (IC), thin film transistors (TFT), flat panel displays, radio frequency identification (RFID) tags, electroluminescent or photoluminescent devices or components, organic light emitting diodes (OLED), backlights of displays, photovoltaic or sensor devices, charge injection layers, Schottky diodes, planarising layers, antistatic films, conducting substrates or patterns, electrode materials in batteries, photoconductors, electrophotographic applications, electrophotographic recording, organic memory devices, alignment layers, or for detecting and discriminating DNA sequences, the improvement wherein said charge-transport, semiconducting, electrically conducting, photoconducting or light-emitting material comprises a compound according to claim 1.

11. An optical electrooptical or electronic device, FET, integrated circuit (IC), TFT, OLED or alignment layer comprising a compound according to claim 1.

12. A TFT or TFT away for flat panel displays, radio frequency identification (RFID) tag, electroluminescent display or backlight, or a FET, IC, TFT or OLED, comprising a compound according to claim 1.

13. A security marking or device comprising a FET or an RFID tag according to claim 11.

14. A compound of formula I $$R^3\text{-}(A)_a\text{-}(B)_b\text{-}(C)_c\text{-}(D)_d\text{-}(E)_e\text{-}R^4 \qquad \text{I}$$

wherein

A, B, C, D and E are independently of each other a TT group of formula II

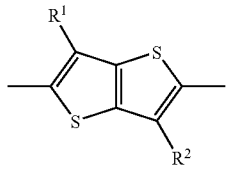

or are selected from phenylene-1,4-diyl that is optionally substituted by one or two $R^1$ groups that are different than H, thiophene-2,5-diyl that is optionally substituted by one or two R1 groups that are different than H, selenophene-2,5-diyl that is optionally substituted by one or two $R^1$ groups that are different than H, and naphthalene-2,6-diyl that is optionally substituted by one or two $R^1$ groups that are different than H, $R^1$ and $R^2$ independently of each other are each H, halogen, P-Sp-, P*-Sp, or straight chain, branched or cyclic alkyl with 1 to 20 C-atoms, which may be unsubstituted, mono- or polysubstituted by F, Cl, Br, I or CN, and wherein one or more non-adjacent $CH_2$ groups are each independently optionally replaced by —O—, —S—, —NH—, —$NR^0$—, —$SiR^0R^{00}$—, —CO—, —COO—, —OCO—, —O—CO—O—, —S—CO—, —CO—S—, —$CX^1$=$CX^2$— or —C≡C— in such a manner that O and/or S atoms are not linked directly to one another, $R^3$ and $R^4$ are independently of each other P-Sp-, P*-Sp-, H, halogen, or straight chain, branched or cyclic alkyl with 1 to 20 C-atoms, which may be unsubstituted, mono- or polysubstituted by F, Cl, Br, I or CN, and wherein one or more non-adjacent $CH_2$ groups are each independently optionally replaced by —O—, —S—, —NH—, —$NR^0$—, —$SiR^0R^{00}$—, —CO—, —COO—, —OCO—, —O—CO—O—, —S—CO—, —CO—S—, —$CX^1$=$CX^2$— or —C≡C— in such a manner that O and/or S atoms are not linked directly to one another, with at least one of $R^3$ and $R^4$ being P-Sp- or P*-Sp-, $X^1$ and $X^2$ are independently of each other H, F, Cl or CN, P is $CH_2$=CH—COO—, $CH_2$=C($CH_3$)—COO—, $CH_2$=CH—, $CH_2$=CH—O—, ($CH_2$=CH)$_2$CH—OCO—, ($CH_2$=CH)$_2$CH—O—

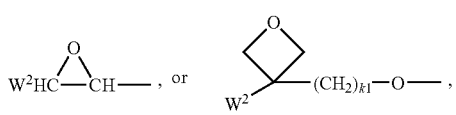

$k_1$ is 0 or 1,

P* is —OH or —O—Si—$R^0R^{00}R^{000}$,

Sp is a spacer group or a single bond, $R^0$, $R^{00}$ and $R^{000}$ are independently of each other H, alkyl with 1 to 12 C-atoms or aryl, and a, b, c and d are independently of each other 0, 1, 2 or 3, with a+b+c+d >0;

wherein the compound comprises two or three TT groups, or the compounds comprise one, two or three TT groups and one, two, three or four groups selected from phenylene-1,4-diyl, thiophene-2,5-diyl, selenophene-2,5-diyl, and naphthalene-2,6-diyl which in each case is optionally substituted by one or two $R^1$ groups that are different than H, and wherein said compound is oxidatively or reductively doped to form a conducting ionic species.

15. A charge injection layer, planarizing layer, antistatic film or conducting substrate or pattern for electronic applications or flat panel displays, comprising a compound according to claim 14.

16. A compound according to claim 6, wherein said compound selected from formula Ia:

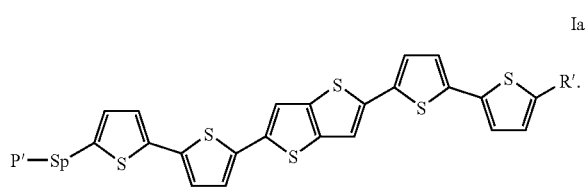

17. A compound according to claim 6, wherein said compound selected from formula Ib:

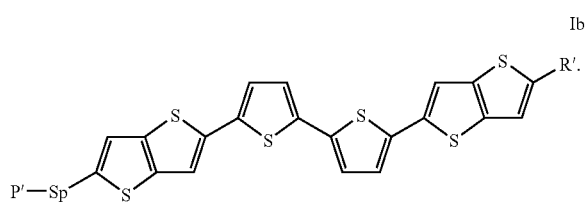

18. A compound according to claim 6, wherein said compound selected from formula Ic:

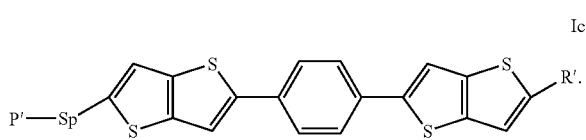

19. A compound according to claim 6, wherein said compound selected from formula Id:

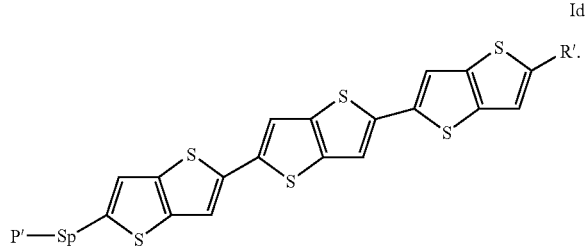

20. A compound according to claim 6, wherein said compound selected from formula Ie:

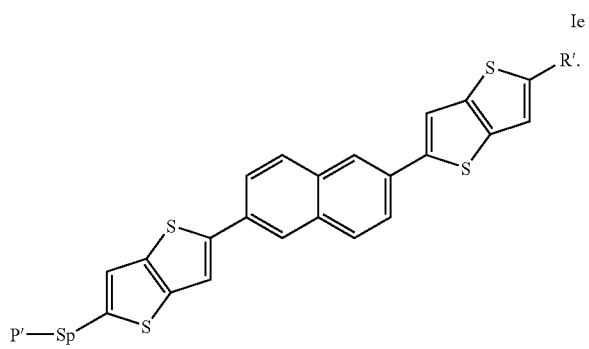

21. A compound according to claim 6, wherein said compound selected from formula If:

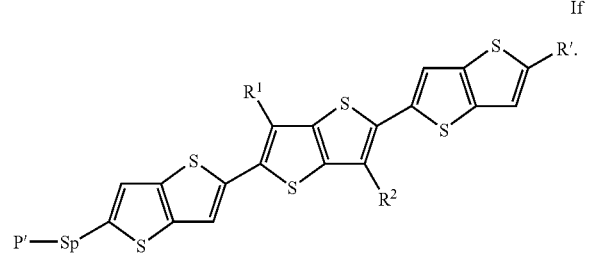

22. A compound according to claim 1, wherein at least one of A, B, C, D and E is phenylene-1,4-diyl that is optionally substituted by one or two groups $R^1$ different from H.

23. A compound according to claim 1, wherein at least one of A, B, C, D and E is thiophene-2,5-diyl that is optionally substituted by one or two groups $R^1$ different from H.

24. A compound according to claim 1, wherein at least one of A, B, C, D and E is selenophene-2,5-diyl that is optionally substituted by one or two groups $R^1$ different from H.

25. A compound according to claim 1, wherein at least one of A, B, C, D and E is naphthalene-2,6-diyl that is optionally substituted by one or two groups $R^1$ different from H.

26. A compound according to claim 1, wherein groups A, B, C, D and E that are not TT are each independently selected from 1,4-phenylene, fluorinated 1,4-phenylene, naphthalene-2,6-diyl, thiophene-2,5-diyl, selenophene-2,5-diyl, fluorinated or alkylated thiophene-2,5-diyl, and fluorinated or alkylated selenophene-2,5-diyl, which in each case are unsubstituted, or mono- or polysubstituted with L, and L is F, Cl, Br, or an alkyl having 1 to 12 C atoms, alkoxy having 1 to 12 C atoms, alkylcarbonyl having up to 12 C atoms, or alkoxycarbonyl having up to 12 C atoms, wherein one or more H atoms are each optionally replaced by F or Cl.

* * * * *

UNITED STATES PATENT AND TRADEMARK OFFICE
CERTIFICATE OF CORRECTION

PATENT NO. : 7,700,643 B2
APPLICATION NO. : 11/570306
DATED : April 20, 2010
INVENTOR(S) : Martin Heeney et al.

It is certified that error appears in the above-identified patent and that said Letters Patent is hereby corrected as shown below:

Column 42, line 47 reads: "selenophene-2,5-diyl, 2,2-dithiophene, fluorinated or"

Should read: -- selenophene-2,5-diyl, 2,2'-dithiophene, fluorinated or --

Signed and Sealed this

Sixteenth Day of November, 2010

David J. Kappos
*Director of the United States Patent and Trademark Office*